United States Patent
Mou et al.

(10) Patent No.: US 10,729,783 B2
(45) Date of Patent: Aug. 4, 2020

(54) HOLLOW SILICA NANOPARTICLES WITH ENCAPSULATED BIOACTIVE INGREDIENTS, PREPARATION PROCESS AND APPLICATIONS THEREOF

(71) Applicant: NATIONAL TAIWAN UNIVERSITY, Taipei (TW)

(72) Inventors: Chung-Yuan Mou, Taipei (TW); Nai-Yuan Kou, Tainan (TW); Si-Han Wu, Taichung (TW); Yi-Ping Chen, Keelung (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/681,207

(22) Filed: Aug. 18, 2017

(65) Prior Publication Data
US 2018/0050115 A1 Feb. 22, 2018

Related U.S. Application Data

(60) Provisional application No. 62/376,920, filed on Aug. 19, 2016.

(51) Int. Cl.
*A61K 47/69* (2017.01)
*A61K 47/02* (2006.01)
*A61K 9/51* (2006.01)
*A61K 38/43* (2006.01)
*A61K 39/00* (2006.01)

(52) U.S. Cl.
CPC ............ *A61K 47/6923* (2017.08); *A61K 9/51* (2013.01); *A61K 9/5115* (2013.01); *A61K 47/02* (2013.01); *A61K 38/43* (2013.01); *A61K 39/00* (2013.01); *C01P 2004/64* (2013.01)

(58) Field of Classification Search
CPC .............. A61K 2300/00; A61K 9/5115; A61K 31/704; A61K 31/7088; A61K 31/7105; A61K 31/713; A61K 47/6923; A61K 9/0019; A61K 9/127; A61K 45/06; A61K 9/1271; A61K 9/5123; A61K 9/5146; A61K 9/5153; A61K 9/5192; A61K 31/192; A61K 31/465; A61K 31/506; A61K 31/513; A61K 33/24; A61K 38/00; A61K 38/17; A61K 38/45; A61K 38/47; A61K 47/02; A61K 47/62; A61K 47/6911; A61K 48/0008; A61K 49/0082; A61K 49/0423; A61K 9/0014; A61K 9/107; A61K 9/5073; A61K 9/5078; A61K 31/495; A61K 31/519; A61K 31/7068; A61K 33/00; A61K 38/08; A61K 38/10; A61K 38/1774; A61K 38/385; A61K 38/43; A61K 38/50; A61K 39/00; A61K 41/0028; A61K 47/10; A61K 47/548; A61K 47/64; A61K 47/6425; A61K 47/6929; A61K 49/0093; A61K 49/225; A61K 9/0009; A61K 9/16; A61K 9/51
See application file for complete search history.

(56) References Cited

U.S. PATENT DOCUMENTS

| | | | |
|---|---|---|---|
| 2004/0180096 A1* | 9/2004 | Prasad ................. | A61K 9/5115 424/490 |
| 2012/0104639 A1* | 5/2012 | Traynor ................. | A01N 25/28 264/4.32 |
| 2012/0201892 A1* | 8/2012 | Li ......................... | A61K 9/0019 424/490 |

FOREIGN PATENT DOCUMENTS

| WO | WO 2001-088540 A1 | 11/2001 | |
|---|---|---|---|
| WO | WO2006/084339 A1 * | 8/2006 | ............. A61K 47/04 |
| WO | WO 2006-084339 A1 | 8/2006 | |
| WO | WO 2016-164987 A1 | 10/2016 | |

OTHER PUBLICATIONS

Chang, Feng-Peng et al., Enzyme encapsulated hollow silica nanospheres for intracellular biocatalysis. ACS Appl Mater Interfaces 2014, 6, 6883-6890.
Chang, Feng-Peng et al., Intracellular implantation of enzymes in hollow silica nanospheres for protein therapy: cascade system of superoxide dismutase and catalase. Functional Nanomaterials for Sustainable Development, vol. 10(22), 2014, 4785-4795.
Extended European Search Report, App. No. 17186824.3, dated Oct. 18, 2017, 9 Pages.
Mashburn, L. T. et al., Tumor Inhibitory Effect of L-Asparaginase, Biochemical and biophysical research communications, 1963, 12(1), 50-55.
Li, Y. et al., Hollow-Structured Mesoporous Materials: Chemical Synthesis, Functionalization and Applications. Adv Mater 2014, 26, 3176-3205.
Tsou, Chieh-Jui et al., Hollow mesoporous silica nanoparticles with tunable shell thickness and pore size distribution for application as broad-ranging pH nanosensor. Microporous and Mesoporous Materials, 2014, 190, 181-188.
Madhav and D. Gupta, A Review on Microemulsion Based System, IJPSR, 2011; vol. 2(8): 1888-1899.

* cited by examiner

*Primary Examiner* — Audrea B Coniglio
(74) *Attorney, Agent, or Firm* — Duane Morris LLP

(57) ABSTRACT

The present invention relates to hollow silica nanoparticles as a drug delivery system loading bioactive ingredients. Particularly, the present invention relates to silica nanoparticles comprising multi-layered silica shells with one or more bioactive ingredients encapsulated within and their applications in drug delivery; and processes of preparing the same.

29 Claims, 8 Drawing Sheets
(2 of 8 Drawing Sheet(s) Filed in Color)

HOLLOW SILICA NANOPARTICLES WITH ENCAPSULATED BIOACTIVE INGREDIENTS, PREPARATION PROCESS AND APPLICATIONS THEREOF

CROSS-REFERENCE TO RELATED APPLICATION

This application is related to, and claims the benefit of, U.S. Provisional Application 62/376,920 filed Aug. 19, 2016, the contents of which are hereby incorporated by reference in their entirety.

FILED OF THE INVENTION

The present invention relates to hollow silica nanoparticles as a drug delivery system enabling loading of bioactive ingredients. Particularly, the present invention relates to silica nanoparticles comprising multi-layered silica shells with one or more bioactive ingredients encapsulated between the shells and their applications in drug delivery.

BACKGROUND OF THE INVENTION

The development of new forms of therapeutics that use macromolecules such as proteins or nucleic acids as therapeutic agents has created a need to develop new and effective approaches of delivering such macromolecules to their appropriate cellular targets. Nanoparticle technology has found application in pharmacology and drug delivery.

Nanocarriers have been developed for macromolecule delivery, including polymers, liposomes, and inorganic nanoparticles such as silica nanoparticles. Among various silica nanomaterials, the hollow silica nanoparticles (HSNs) have been deemed to have great potential as drug delivery systems due to their unique physical/chemical properties, such as large pore volume, chemical/thermal stability, high loading capacity, adjustable surface properties and excellent biocompatibility. Different from common solid mesoporous silica nanoparticles (MSNs), HSNs can encapsulate species that are large in size (such as bioactive ingredients) and exhibit higher loading capacity of said large species due to the unique morphology, i.e., thin porous shell and hollow interior space, which in turn enhance the efficacy of applications in catalysis, biomedicine, etc. The morphology and characteristics of HSNs greatly depend on the synthetic strategies, which differ from application to application.

Hard-templating methods, known as conventional methods for synthesizing hollow silica nanoparticles, utilize solid and rigid particles (such as polystyrene particles) as a core template, and the material of the template is heterogeneous to silica. Given this, the core template can be etched by calcination, solvent dissolution or other means to leave a hollow space inside the closed silica shell (Li, Y.; Shi, J. *Hollow-structured mesoporous materials: chemical synthesis, functionalization and applications. Adv Mater* 2014, 26, 3176-3205). Though the homogeneity of the nanoparticle size, nanoparticle shape and dimension of the cavity can be precisely controlled, such methods require a multistep synthetic process as well as a tedious template etching procedure, which is time-consuming and/or complicated.

Soft-templating methods also utilize the concept of etching the core template from a core-shell structure to form hollow silica nanoparticles, but the core template is "softer" than those applied in the hard-templating methods. For example, the soft core templates can be flexible liquid "particles," such as micelles, emulsion, vesicles consisting of materials heterogeneous silica, or even gas bubbles. However, it is generally considered that HSNs prepared by these methods have an irregular appearance and wider particle size distribution due to the flexibility of the soft template. For example, special Kippah-like HSNs will be formed if the oil in the oil-in-water (O/W) emulsion escapes through mesopores before the silica shell structure becomes rigid (Tsou, C.-J.; Hung, Y.; Mou, C.-Y. *Hollow mesoporous silica nanoparticles with tunable shell thickness and pore size distribution for application as broad-ranging pH nanosensor. Microporous and Mesoporous Materials* 2014, 190, 181-188).

However, the bioactive ingredients cannot be loaded prior to the template etching procedure because said procedure would likely destroy the activity thereof.

In addition to the above-mentioned methods, structural-difference selective etching methods provide a different concept for synthesizing hollow silica nanoparticles. In such methods, different silica sources are used to form silica nanoparticles having structural difference within the nanoparticles, i.e., the structure would exhibit different strengths at different sites, in particular the inner layers would be more fragile than the outer layers. Such phenomenon was found in some sol-gel processes, including the most general Stöber method. Hence, by selectively and gently removing the fragile parts of the nanoparticles, a hollow space would be created. The selective removal of the fragile parts could be relatively controllable, in particular when the level of structural difference is raised by specific designs during the fabrication of the silica nanoparticles.

By taking advantages of synthesis in a microemulsion system, a method of de novo enzyme encapsulation in HSNs has been disclosed by Chang, et. al. (*Enzyme encapsulated hollow silica nanospheres for intracellular biocatalysis. ACS Appl Mater Interfaces* 2014, 6, 6883-6890; *Intracellular implantation of enzymes in hollow silica nanospheres for protein therapy: cascade system of superoxide dismutase and catalase. Small* 2014, 10, 4785-4795). However, though structural-difference selective etching methods may somehow prevent the problems confronted by using hard- or soft-templating methods, the yield of the hollow silica nanoparticles is quite low (up to about 10 mg/20 mL oil). In addition, the nanoparticles prepared by these methods still tend to aggregate, which is a significant problem to be solved.

Hence, there is still needs for improved hollow silica nanoparticles as drug delivery systems and a simple, cost-effective way to synthesize such hollow silica nanoparticles.

SUMMARY OF THE INVENTION

In order to overcome the problems confronted in the art, the subject application provides the following solutions.

A silica nanoparticle, which belongs to a hollow silica nanoparticle (HSN) and in particular can act as a drug delivery system, is provided, First, the subject application provides a silica nanoparticle, comprising multi-layered silica shells, wherein each shell has meso-pores and encloses a closed hollow space, wherein optionally the innermost hollow closed space has a solid silica core; and one or more bioactive ingredients encapsulated within the space, wherein the bioactive ingredient has a size larger than the pore size of the shell encapsulating it, and wherein the bioactive ingredient in each space may be the same or different.

Second, the subject application also provides a method for preparing a silica nanoparticle, comprising the steps of:

(a) any one of steps (a-1) and (a-2):
  (a-1) providing an oil phase, a surfactant, an alkoxysilane and/or silicate source, an aqueous phase optionally containing one or more bioactive ingredients and optionally a co-surfactant to form a water-in-oil (W/O) microemulsion; and
  (a-2) providing an oil phase, a surfactant, an alkoxysilane and/or silicate source and optionally a co-surfactant to form a mixture;
(b) adding an initiating reagent to the W/O microemulsion of (a-1), or adding an aqueous initiating reagent to the mixture of (a-2) to form a W/O microemulsion, and then forming a silica nano-core which links the bioactive ingredient on the surface thereof and/or encapsulates the bioactive ingredient therein;
(c) providing an aqueous phase containing a bioactive ingredient;
(d) introducing an alkoxysilane and/or silicate source to form an additional silica layer enclosing the silica nano-core of (b);
(e) optionally repeating the steps (c) and (d) one or more times;
(f) performing a destabilizing condition to destabilize the W/O microemulsion and collecting the resulting particle thus formed from the microemulsion; and
(g) dispersing the particle collected in step (f) in an aqueous washing phase to obtain the silica nanoparticle;
wherein the alkoxysilane and/or silicate source in steps (d) and (e) and optionally that in step (a) comprise at least one organo-alkoxysilane, and
wherein the size of the bioactive ingredients is larger than the pore size of the silica shell encapsulating the same.

The subject application also provides the products prepared by the method as described above.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIGS. 1(A) to 1(F) are various views of TEM images of the control silica nanoparticles and the exemplary inventive embodiment silica nanoparticles. FIG. 1(A). An image of an exemplary nanoparticle embodiment. FIG. 1(B). An image of an exemplary nanoparticle embodiment. FIG. 1(C). An image of an exemplary nanoparticle embodiment. FIG. 1(D). An image of an exemplary nanoparticle embodiment. FIG. 1(E). An image of an exemplary nanoparticle embodiment. FIG. 1(F). An image of an exemplary nanoparticle embodiment.

FIGS. 2(A) and 2(B) are nitrogen sorption isotherms of the exemplary inventive silica nanoparticles. FIG. 2(A) is an image of the nitrogen sorption isotherm of certain exemplary inventive silica nanoparticle embodiment. FIG. 2(B) is an image of the nitrogen sorption isotherm of certain exemplary inventive silica nanoparticle embodiment.

FIGS. 3(A) and 3(B) show the results of enzyme activity tests of ASNase, PEGs-ASNase and the inventive silica nanoparticles. FIG. 3(A) shows the results with ASnase and PEGs-Asnase. FIG. 3(B) show the results with Asnase.

FIG. 4 shows the results of cytotoxicity assay of MOLT-4 leukemic cell line with PEGs-ASNase, control silica nanoparticles and the inventive silica nanoparticles.

FIGS. 5(A) and 5(B) show the results of cellular uptake efficiency assay (in MOLT-4 cells) based on the inventive silica nanoparticles. FIG. 5(A) shows % cell uptake. FIG. 5(B) shows MFI between two groups are similar.

As shown in FIG. 6, the MOLT-4 cells treated with free ASNase FIG. 6D) and PEGs-ASNase@PEG-HSN 15 FIG. 6E) and 17 FIG. 6F) exhibited apoptotic signs compared to controls FIG. 6A), FIG. 6B), and FIG. 6C).

DETAILED DESCRIPTION OF THE INVENTION

Figure 1A:
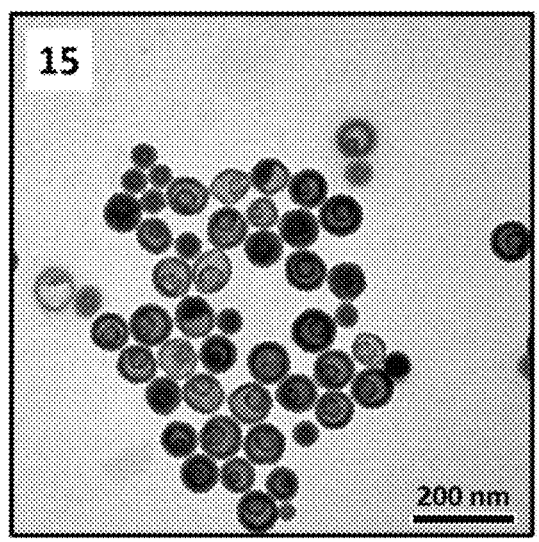
Figure 1B:
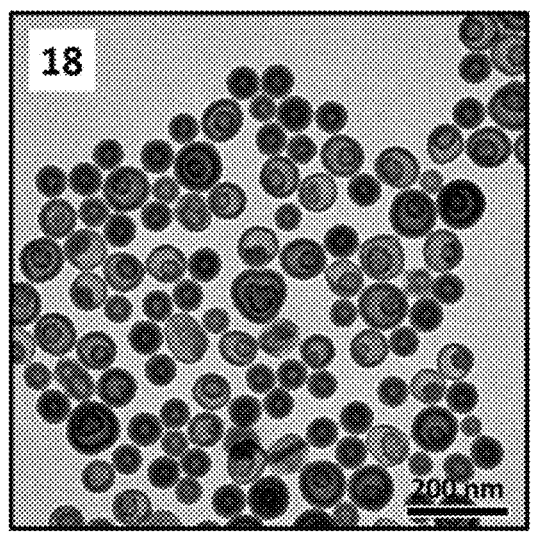
Figure 1C:
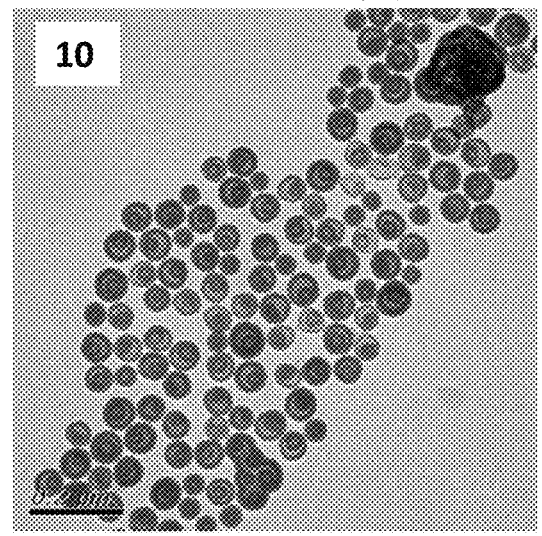
Figure 1D:
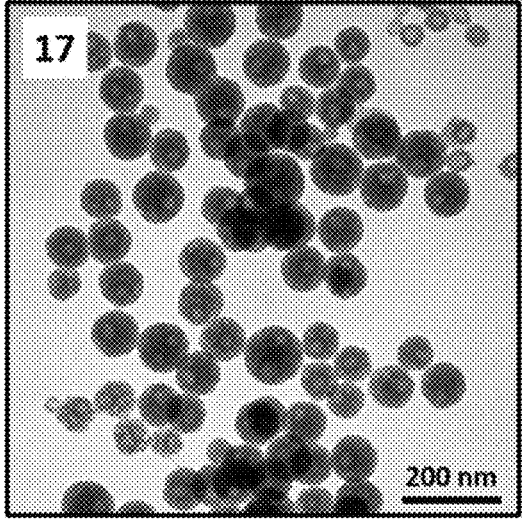
Figure 1E:
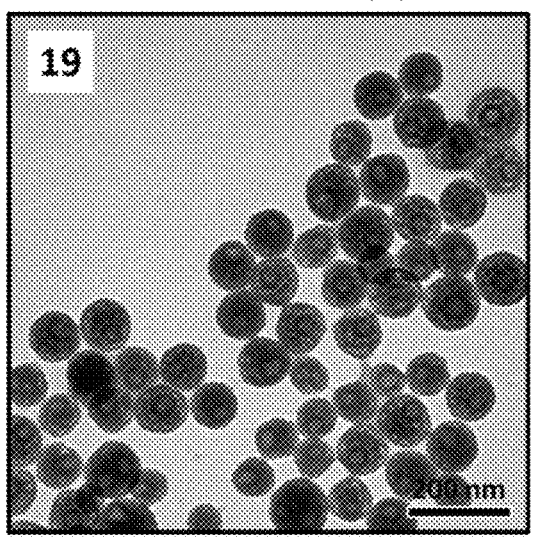
Figure 1F:
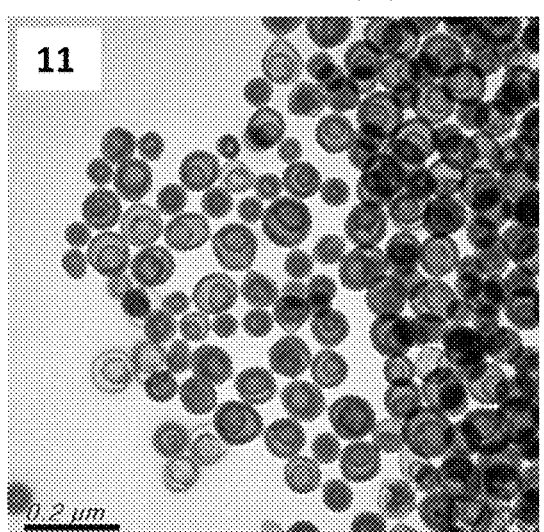

In order to facilitate the understanding of the disclosure herein, terms as used herein are hereby defined below.

In the context of the specification and the claims, the singular forms "a", "an" and "the" include plural referents, unless specifically indicated otherwise. Unless otherwise stated, any and all examples or exemplary language (e.g., "such as") provided herein are merely used for better illustration of the present invention, instead of limiting the scope of the present invention.

It is to be understood that any numerical range recited in this specification is intended to include all sub-ranges encompassed therein. For example, a range from "50 to 70° C." includes all sub-ranges and specific values between the stated minimum value of 50° C. and the stated maximum value of 70° C., inclusive, e.g. from 58° C. to 67° C., and from 53° C. to 62° C., 60° C. or 68° C. Since the numerical ranges disclosed are continuous, they contain each numerical value between the minimum and maximum value. Unless otherwise specified, the various numerical ranges indicated in this specification are approximate.

In the present invention, the term "about" refers to an acceptable deviation of a given value measured by a person of ordinary skill in the art, depending, in part, on how to measure or determine the value.

In the present invention, unless particularly specified, the prefix "nano-" as used herein means a size of about 300 nm or less. Unless particularly specified, the prefix "meso-" as used herein, unlike the definition suggested by IUPAC, means a size of about 5 nm or less.

In the present invention, the term "silane" as used herein refers to derivatives of $SiH_4$. Normally, at least one of the four hydrogens is replaced with substituents such as alkyl, alkoxyl, amino, etc. as described below. The term "alkoxysilane" as used herein refers to a silane having at least one alkoxyl substituent directly bonded to the silicon atom. The term "organo-alkoxysilane" as used herein refers to a silane having at least one alkoxyl substituent and at least one hydrocarbyl substituent directly bonded to the silicon atom. The term "silicate source" as used herein refers to substances which can be deemed as a salt form or an ester form of orthosilicic acid, for example sodium orthosilicate, sodium metasilicate, tetraethyl orthosilicate (tetraethoxy silane, TEOS), tetramethyl orthosilicate, tetrapropyl orthosilicate. Optionally, the hydrocarbyl substituent can be further substituted or interrupted with a heteroatom.

In the present invention, the term "hydrocarbyl" as used herein refers to a mono-valent radical derived from hydrocarbons. The term "hydrocarbon" as used herein refers to a molecule that consists of carbon and hydrogen atoms only. Examples of the hydrocarbons include, but are not limited to, (cyclo)alkanes, (cyclo)alkenes, alkadienes, aromatics, etc. When the hydrocarbyl is further substituted as mentioned above, the substituent can be halogens, amino groups, a hydroxy group, a thiol group, etc. When the hydrocarbyl is interrupted with a heteroatom as mentioned above, the heteroatom can be S, O or N. In the present invention, a hydrocarbyl preferably comprises 1 to 30 C atoms.

In the present invention, the term "alkyl" refers to a saturated, straight or branched alkyl, which comprises preferably 1-30 carbon atoms, and more preferably 1-20 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, iso-heptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present invention, the term "alkoxyl" or "alkoxy" as used herein means a group having a formula "—O-alkyl," wherein the definition of the "alkyl" in said formula has the meaning of "alkyl" as stated above.

In the present invention, the term "cycloalkyl" as used herein means a saturated or partially unsaturated cyclic carbon radical containing 3 to 10 ring carbon atoms and more preferably 3 to 8 ring carbon atoms, and optionally an alkyl substituent(s) on the ring. Examples of cycloalkyl include, but are not limited to, cyclopropyl, cyclopropenyl, cyclobutyl, cyclopentyl, cyclohexyl, 2-cyclohexen-1-yl, and the like.

In the present invention, the term "halogen" or "halo" denotes fluorine, chlorine, bromine or iodine.

In the present invention, the term "amino" as used herein means a functional group of the formula —NR$_1$R$_2$, wherein R$_1$ and R$_2$ each independently represent hydrogen or a hydrocarbyl group as defined above.

In the present invention, the term "aqueous phase" as used herein means a phase substantively miscible with water. Examples of the aqueous phase include, but are not limited to, water per se, aqueous buffers, aqueous dimethylsulfoxide (DMSO) solutions, aqueous alkanolic solutions, etc. The aqueous phase may be adjusted to be acidic, neutral or alkaline, based on the demand of the synthesis and/or the stability of the substance present in the aqueous phase.

In the present invention, the term "oil phase" as used herein means a phase substantively immiscible with the aqueous phase as mentioned above. Examples of the oil phase include, but are not limited to, liquid, substituted or unsubstituted (cyclo)alkanes, such as hexane, decane, octane, dodecane, cyclohexane, etc.; substituted or unsubstituted aromatic solvents, such as benzene, toluene, xylene, etc.

In the present invention, the term "bioactive ingredient" as used herein refers to substance having an activity in an organism. Examples of the bioactive ingredient include, but are not limited to, an enzyme, a protein drug, an antibody, a vaccine, an antibiotic or a nucleotide drug.

Hollow Silica Nanoparticles Encapsulating Bioactive Ingredient

In one aspect, the invention provides a silica nanoparticle comprising: multi-layered silica shells, wherein each shell has meso-pores and encloses a closed hollow space, optionally the innermost hollow closed space has a solid silica core with meso-pores; and one or more bioactive ingredient encapsulated within the space, wherein the bioactive ingredient has a size larger than the pore size of the shell encapsulating it, and wherein the bioactive ingredient in each space may be the same or different.

In one embodiment of the silica nanoparticle of the present invention, it has a core-shell structure with a nano-core and at least one closed shell, and there is a space between the nano-core and shell(s). In one embodiment, the nano-core is solid. In another embodiment, the nano-core is hollow and thus can also be deemed as a hollow closed shell. In one embodiment, the silica nanoparticle has a hollow nano-core and one outer shell, i.e., two closed shells in total. In another embodiment, the silica nanoparticle has a solid nano-core and one outer closed shell. In one embodiment, the silica nanoparticle has a hollow core and two or more closed shells, i.e., three or more closed shells in total. In another embodiment, the silica nanoparticle has a solid nano-core and two or more outer closed shells.

The particle size of a hollow silica nanoparticle of the present invention is defined by the outer diameter of the outermost closed shell. In one embodiment, the silica nanoparticle of the present invention has a particle size ranging from about 20 mm to about 500 nm, preferably ranging from about 20 nm to 150 nm, more preferably less than 100 nm or less than 30 nm.

In one embodiment, the shells of the silica nanoparticle of the present invention each independently have a thickness of at least about 2 nm, at least about 3 nm or at least about 5 nm; and at most about 15 nm, at most about 12 nm or at most 10 nm; or the thickness falls in a range formed by any combination of the aforementioned upper and lower limits.

The nano-core and shells of the hollow silica nanoparticle of the present invention are mesoporous, and the meso-pores have a size of about 5 nm or less, preferably 3 nm or less, more preferably 2 nm or less.

In one embodiment, each shell encloses a closed hollow space, and the distance between the nano-core and the shell or between the shells is less than 75 nm, preferably ranges from about 2 nm to 75 nm, more preferably ranges from about 2 nm to 50 nm.

In one embodiment, the outer and inner surfaces of the shell(s) can be independently unmodified or modified. Modifications of the surface of the shells can be made de novo or can be post-modifications. Examples of the modification can be, but are not limited to, hydrophilic modifications, such as poly(ethylene glycol) (PEG) modification, polyethylenimine (PEI) modification, 3-(trihydroxysilyl) propyl methylphosphonate (THPMP) modification, N-(trimethoxysilylpropyl)ethylenediamine triacetic acid (EDTAS) N-[3-(trimethoxysilyl)propyl]ethylenediamine modification, N-[3-(trimethoxysilyl)propyl]-N,N,N-trimethylammonium (TA-trimethoxysilane) modification, (3-mercatopropyl)trimethoxysilane (MPTMS) modification, zwitterionic silane modification; specificity modifications, such as modifications with biomarkers, for example antibody modifications, linker modifications, tumor-targeting ligand modification, etc.; or non-specific activity modifications, such as modifications of surface properties of the shell, for example modification of the charge types or distribution, etc.

The hollow silica nanoparticle comprises one or more bioactive ingredients encapsulated within the space. In one embodiment, the bioactive ingredients are encapsulated between each shell. In one embodiment, the hollow silica nanoparticle has a solid nano-core and one outer closed shell, and the bioactive ingredient is encapsulated between the nano-core and the shell. In another embodiment, for the nano-core and the outermost shell, the bioactive ingredient may be linked to the surface thereof. In one embodiment, the bioactive ingredients have a size larger than that of the meso-pores. In further embodiments, additional therapeutic agent(s) having a size less than or equal to the meso-pores can be loaded de novo or passively loaded into the hollow silica nanoparticle.

In one embodiment, the bioactive ingredient can be selected from those that are water soluble or that have surface modification making it capable of dispersing or dissolving in an aqueous phase. In one embodiment, the bioactive ingredient is an enzyme, a protein drug, an antibody, a vaccine, an antibiotic or a nucleotide drug. Examples of the enzyme include, but are not limited to, agalsidase, imiglucerase, taliglucerase, velaglucerase, alglucerase, sebelipase, laronidase, idursulfase, elosulfase, galsulfase, alglucosidase, asparaginase, glutaminase, arginine deiminase, arginase, methioninase, cysteinase, homocysteinase, phenylalanine hydroxylase, phenylalanine ammonia lyase, urate oxidase, catalase, horseradish peroxidase, superoxide dismutase or glutathione peroxidase.

Examples of the additional therapeutic agent include, but are not limited to, doxorubicin, curcumine, paclitaxel, ixabepilone, gemcitabine, irinotecan, SN-38, 5-FU, daunorubicin, docetaxel, etc.

Without being bound to theory, the silica nanoparticle of the present invention exhibits a BET surface area of about 400 m$^2$/g or less, for example 50 to 200 m$^2$/g, depending on the types and amounts of the encapsulated bioactive agents, the number of multi layers and the modification on the surface of the shells of the silica nanoparticle.

The silica nanoparticle of the present invention can be prepared by, for example but not limited thereto, a structural-difference selective etching method. Preferably, the silica nanoparticle of the present invention is not calcined during preparation. Given this, the silica nanoparticle of the present invention preferably has an organosilica residue(s), e.g., organo-alkoxysilane residues, within or on the surface of the nano-core and the closed shell(s).

Method for Preparing Silica Nanoparticles Encapsulating Bioactive Ingredient

The present invention also provides a method for preparing a silica nanoparticle which encapsulates a bioactive ingredient therein. The method comprises the following steps:

(a) any one of steps (a-1) and (a-2):
  (a-1) providing an oil phase, a surfactant, an alkoxysilane and/or silicate source, an aqueous phase optionally containing one or more bioactive ingredients and optionally a co-surfactant to form a water-in-oil (W/O) microemulsion; and
  (a-2) providing an oil phase, a surfactant, an alkoxysilane and/or silicate source and optionally a co-surfactant to form a mixture;
(b) adding an initiating reagent to the W/O microemulsion of (a-1), or adding an aqueous initiating reagent to the mixture of (a-2) to form a W/O microemulsion, and then forming a silica nano-core which links the bioactive ingredient on the surface thereof and/or encapsulates the bioactive ingredient therein;
(c) providing an aqueous phase containing a bioactive ingredient;
(d) introducing an alkoxysilane and/or silicate source to form an additional silica layer enclosing the silica nano-core of (b);
(e) optionally repeating the steps (c) and (d) one or more times;
(f) performing a destabilizing condition to destabilize the W/O microemulsion and collecting the resulting particle thus formed from the microemulsion; and
(g) dispersing the particle collected in step (f) in an aqueous washing phase to obtain the silica nanoparticle;

wherein the alkoxysilane and/or silicate source in steps (d) and (e) and optionally that in step (a) comprise at least one organo-alkoxysilane, and wherein the size of the bioactive ingredients is larger than the pore size of the silica shell encapsulating the same.

In step (a-1), the amounts of the oil phase, surfactant and aqueous phase are selected such that a water-in-oil (W/O) microemulsion will form after mixing these substances. In general, the amount oil phase is much larger than that of the surfactant and aqueous phase to form a W/O microemulsion. The means of forming a W/O microemulsion are generally known in the art, and the means which are not detrimental to the activity of the bioactive ingredient can be utilized in the present invention. The definitions and examples of the oil phase, aqueous phase, bioactive ingredient, alkoxysilane and silicate source have been described in detail above.

The surfactants used for forming a W/O microemulsion are commonly used and readily known in the art. Preferably, non-ionic surfactants are used in the present invention. Examples of the non-ionic surfactant include, but are not limited to, poly(oxyethylene)nonylphenyl ether (e.g., CO-520), polyoxyethylene glycol sorbitan alkyl ester, polyethylene glycol alkyl ether, glucoside alkyl ether, polyethylene glycol octylphenyl ether, polyethylene glycol alkylphenyl ether, glycerol alkyl ester, polypropylene glycol alkyl ethers, poloxamers, cocamide monoethanolamine (cocamide MEA), cocamide diethanolamine (cocamide DEA), lauryldimethylamine oxide, polyethoxylated tallow amine, etc.

Optionally, a co-surfactant can be used to facilitate the formation of or to stabilize the microemulsion. Examples of the co-surfactant include, but are not limited to alkanols, such as hexyl alcohol; polyethylene glycol 400 (PEG 400), PEG 600, etc.

Co-solvents in small quantities can be introduced into the aqueous phase to achieve well dispersion or dissolution of the bioactive ingredients, if necessary. Examples of the co-solvent include, but are not limited to, dimethyl sulfoxide (DMSO), ethanol, PEI, PEG, poly-lysine, poly-arginine, arginine solution, glutamate solution, argingine-glutamate mixture solution, monosaccharides, disaccharides, oligosaccharides, polysaccharides, sodium chloride, potassium chloride, sodium sulfate, Tris buffer, phosphate buffer.

In one embodiment, the aqueous phase optionally containing one or more bioactive ingredients is provided before the alkoxysilane and/or silicate source in step (a-1). In another embodiment, the alkoxysilane and/or silicate source is provided before the aqueous phase optionally containing one or more bioactive ingredients in step (a-1). In yet another embodiment, the aqueous phase optionally containing one or more bioactive ingredient and the alkoxysilane and/or silicate source are simultaneously provided in step (a-1). Namely, the order of the introduction of the aqueous phase optionally containing one or more bioactive ingredients and the alkoxysilane and/or silicate source in step (a-1) can be reversed or done simultaneously.

In another embodiment, step (a-2) is adopted; that is, an oil phase, a surfactant, an alkoxysilane and/or silicate source and optionally a co-solvent are provided to form a mixture. Next, an initiating reagent is added to initiate the formation of silica, as step (b). In step (b), the initiating reagent is a substance which can trigger the reaction to form silica. Examples of the initiating reagent include, but are not limited to, acidic substances, such as acids or acidic aqueous solutions, for example hydrochloric acid, sulfuric acid, etc.; alkaline substances, such as bases or alkaline aqueous solutions, such as aqueous ammonia, an aqueous sodium hydroxide solution; and ionic sources, such as salts, solutions of salts and buffers, for example sodium fluoride, phosphate buffers, etc. In one embodiment, when step (a-2) is adopted, the initiating reagent introduced in step (b) is an aqueous initiating reagent, which triggers not only the formation of a W/O microemulsion but also the reaction to form silica. Upon initiation of the reaction, a silica nano-core is formed, wherein the bioactive ingredient is linked to the surface of the silica nano-core and/or encapsulated inside the silica nano-core.

In one embodiment, when aqueous phase containing no bioactive ingredient is used in step (a-1), the silica nano-core formed in step (b) will not link to and/or encapsulate any bioactive ingredient de novo. In one embodiment, when an aqueous phase containing a bioactive ingredient is used in step (a-1), the silica nano-core formed in step (b) will link to and/or encapsulate the bioactive ingredient.

In the subsequent steps (c) and (d), a further aqueous phase containing a bioactive ingredient and a further alkoxysilane and/or silicate source are introduced, respectively. Then, a further silica layer enclosing the silica nano-core is formed, making the silica particle two-layered.

Upon forming a two-layered silica particle, the operations of steps (c) and (d) can be optionally further repeated one or more times, as step (e), to form a number of additional layers (such as a third, fourth, . . . layer) enclosing the existing silica particle.

Then, a condition of destabilizing the W/O microemulsion is performed as step (f) and the resulting particles thus formed from the microemulsion are collected. Examples of the destabilizing condition include, but are not limited to, adding a destabilizing agent, such as an alcohol, excess surfactant(s), etc. The collected particles can be quickly rinsed with water, alkanols (such as $C_{1-3}$ alcohol, e.g., ethanol, isopropyl alcohol, etc.) or aqueous alkanolic solutions.

Finally, the particle collected in step (f) is dispersed in an aqueous washing phase as step (g) to obtain the silica nanoparticle as claimed. The washing phase can be water, alkanols (such as $C_{1-3}$ alcohol, e.g., ethanol, isopropyl alcohol, etc.) or aqueous alkanolic solutions.

The nano-core and shell(s) produced by the present method have meso-pores on the surface. Without being bound to the theory, the size of the meso-pores can be adjusted by using different types of surfactants, co-surfactants and/or alkoxysilane and/or silicate source(s), or the amounts of the alkoxysilane and/or silicate source(s).

Preferably, the ratio of the total volume of the surfactant and co-surfactant to the total volume of the alkoxysilane and/or silicate source(s) used in the method is controlled. In one embodiment, said ratio ranges from about 3.5:1 to about 9.0:1, preferably 4.5:1 to about 8.0:1, more preferably from about 5.5:1 to about 7.5:1.

In one embodiment, when step (e) is employed, i.e., the further aqueous phase(s) containing a bioactive ingredient and alkoxysilane and/or silicate source(s) are provided and introduced, the number of shells can be adjusted in step (g) depending on the manufacturer's desire. The factors determining the number of the shells include the times of repeating steps (c) and (d), the types of the alkoxysilane and/or silicate source(s) as used in these steps, the time of washing in step (g), the temperature for conducting the washing in step (g), etc. For example, when silica nanoparticles having a two-layered structure, step (e) should be conducted at least once. In one embodiment, step (e) is conducted once and silica nanoparticles having only one layer are produced after washing. In addition, the temperature and/or time of washing may be determined based on the susceptibility of the alkoxysilane and/or silicate source(s) to the washing. For example, when the temperature is higher, the effect of washing may be more evident, and vice versa. The temperature for washing may be, for example, up to 80° C., up to 70° C., etc., or may be ambient (20° C., 25° C. or 37° C.). In one embodiment, the silica nano-core remains solid after the washing, while one or more shells enclosing the silica nano-core and closed hollow space are formed. In one embodiment, each layer, including the silica nano-core, is a shell enclosing closed a hollow space.

In one embodiment, the alkoxysilane and/or silicate sources used in steps (a), (d) and (e) are each independently the same or different. In one embodiment, the alkoxysilane and/or silicate source comprises tetraethoxysilane (TEOS), tetramethoxysilane (TMOS), sodium silicate or a mixture thereof. In one embodiment, the organo-alkoxysilane is 2-[methoxy(polyethyleneoxy)propyl]-trimethoxysilane (PEG-trimethoxysilane), 3-aminopropyltrimethoxysilane (APTMS), propyl triethoxy silane, butyl trimethoxy silane, octyl trimethoxy silane, diphenyl diethoxy silane, n-octyl triethoxy silane, mercapto propyl trimethoxy silane, chloro methyl trimethoxy silane, isobutyl triethoxy silane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediamine triacetic acid (EDTAS), (3-trihydroxysilyl)propyl methylphosphonate (THPMP), methyltriacetoxysilane (MTAS), N-[3-(trimethoxysilyl)propyl]ethylenediamine, trimethoxysilylpropyl (polyethlenimine), N-trimethoxysilylpropyl-N,N,N-trimethylammonium chloride, (3-mercatopropyl) trimethoxysilane (MPTMS), zwitterionic silane or a mixture thereof. In one embodiment, the alkoxysilane and/or silicate source is a mixture of TEOS and APTMS, a mixture of THPMP, APTMS and TEOS or a mixture of EDTAS, APTMS and TEOS. In one embodiment, the alkoxysilane and/or silicate source used in step (a) is a mixture of THPMP, APTMS and TEOS; or a mixture of EDTAS, APTMS and TEOS. In one embodiment, the alkoxysilane and/or silicate source used in step (d) and/or (e) is a mixture of APTMS and TEOS. The present invention also provides a silica nanoparticle prepared by any of the methods as described above.

The following examples are provided to make the present invention more comprehensible to those of ordinary skill in the art to which the present invention pertains, but are not intended to limit the scope of the invention.

EXAMPLES

Materials, Methodologies and Test Models
PEG Modified ASNase (PEGs-ASNase)

As known in the art, asparaginases ("ASNases") are useful in treating patients with acute lymphoblastic leukemia (ALL). Hence, ASNase is used as an example of the bioactive ingredient of the present invention. For increasing the solubility of ASNase in aqueous phase, we modified the surface of ASNase with SCM-PEG-MPTMS moiety; the product was hereinafter referred to as PEG-ASNase. Without being bound to theory, it is believed that PEG-ASNase may be conjugated with the alkoxysilane and/or silica source and such conjugation may be helpful for subsequent encapsulation of PEG-ASNase. Preparation of PEGs-ASNase is illustrated as follows: maleimide-poly(ethylene glycol)-succinimidyl ester (MAL-PEG-SCM) (6.4 mg) and (3-mercatopropyl)trimethoxysilane (MPTMS) (5 μL) are mixed with ASNase (1 mg), the mixture is dissolved in a $NaH_2PO_4$ buffer solution (50 mM, pH 7.8) and the solution is stirred at 4° C. for 6 hrs. Then, the product (PEGs-ASNase) is purified by dialyzing excess MAL-PEG-SCM, MPTMS or RITC in $NaH_2PO_4$ buffer solution (50 mM, pH 7.8) at 4° C. for 2 days to remove these excess agents. Finally, the PEGs-ASNase is concentrated with Amicon® Ultra filters.

Fluorophore-Labeled ASNase

For assays based on fluorescence, ASNase may be conjugated with a fluorophore; here, for example, rhodamine isothiocyanate (RITC) or fluorescein isothiocyanate (FITC). Synthesis of RITC-labeled PEGs-ASNase can be accomplished by a method similar to that of synthesizing PEGs-ASNase, while RITC was introduced together with MAL-PEG-SCM and MPTMS, and it can also be covalently conjugated onto ASNase.

Transmission Electron Microscopy (TEM)

Transmission electron microscopy (TEM) is used to evaluate and directly examine the appearance of the silica nanoparticles, such as the size of each layer, the number and thickness of the shells, the dimension of the closed hollow space, etc. The TEM images were taken on a Hitachi H-7100 transmission electron microscope operating at an accelerated voltage of 75 kV, and samples were dispersed in ethanol and sonicated for 30 seconds before deposit on carbon-coated copper grids and dried in air.

Dynamic Light Scattering (DLS)

Size measurements of the silica nanoparticles in different solution environments were performed with dynamic light scattering (DLS) on a Malvern Zetasizer Nano ZS (Malvern, UK). The concentration of the silica nanoparticles are 0.2-0.3 mg/mL. The (solvated) particle sizes in different solutions were analyzed: $H_2O$ (pH6~7), Dulbecco's Modified Eagle Medium (DMEM) with 10% FBS, Dulbecco's Modified Eagle Medium (DMEM) with 20% FBS, RPMI Media 1640 with 10% FBS and PBS buffer solution (pH7.4).

ASNase Activity Tests for Characterization

Quantitative estimation of ASNase activity was carried out by the Nesslerization method through the detection of ammonia (Mashburn, L. T. and Wriston, J. C., *Biochemical and biophysical research communications*, 1963, 12(1), 50-55). In particular, ASNases or silica nanoparticles containing ASNases were respectively centrifuged and dispersed in 200 μL of 0.05 M, pH 8.6 Tris buffer, and then incubated with its substrate (i.e., 1.7 mL of 0.01 M L-asparagine in 0.05 M Tris buffer, pH 8.6; the L-asparagine was purchased from Pro-Spec) at 37° C. for 10 minutes to 72 hours; a parallel control group without the addition of ASNase was incubated under the same condition. The reaction was quenched by adding 100 μL of 1.5 M trichloroacetic acid (TCA). The sample was then subjected to centrifugation, and 500 μL of the supernatant was diluted with 7 mL of D.I. water (18.2 MΩ resistivity) and mixed with 1 mL of Nessler's reagent (purchased from Merck; containing potassium hydroxide and potassium tetraiodomercurate) to form a yellowish solution (containing ammonia). The mixture was incubated at room temperature for 10 minutes, and the absorbance at 480 nm was measured by a spectrophotometer. Ammonium sulfate was used as a standard to establish the calibration curve. 1 Unit (U) of ASNase is defined as the amount of μmole of ammonia per minute per milligram produce by the ASNase at 37° C., pH8.6.

Synthetic Example 1

Synthesis of PEGs-HSN

Example 1A

PEGs-ASNase@PEG-HSN 15

Twenty (20) mL decane (as an oil phase), 3.5 mL CO-520 (as a surfactant) and 1.1 mL hexyl alcohol (as an optional co-surfactant) were mixed. Then, 200 μL of TEOS and 25 μL of ethanolic APTMS solution (from a stock solution of 200 μL APTMS in 1.4 mL ethanol) (as an alkoxysilane and/or silica source) were added into the mixture and the mixture was stirred at 20° C. Fifteen minutes later, 500 μL of $NH_4OH$ (28-30 wt. %) (as an initiating reagent) was added dropwise to the mixture to initiate the hydrolysis of the silica alkoxysilane and/or silica source and form a silica nano-core. After 2 hrs., 700 μL of $H_2O$ (with 2385.2 μg of PEGs-ASNase therein, as an aqueous phase) was slowly added to the microemulsion. Further 10 minutes later, 300 μL of TEOS and 100 μL of ethanolic APTMS solution (as an alkoxysilane and/or silica source) were added to the microemulsion and the microemulsion was stirred for 12 hrs. at 20° C. to form a second silica layer enclosing the silica nano-core. Then, 500 μL of PEG-trimethoxysilane and 50 μL of TEOS were added to both of them to modify the surface of the silica nanoparticles. After 24 hrs., 95% ethanol was used to destabilize the microemulsion system. The resulting particles were collected by centrifugation at 15,500 rpm for 25 minutes and quickly rinsed with ethanol twice. Then, the particles were transferred into 200 mL D.I. water for washing at 50° C. for 2 hrs. Finally, the hollow silica nanoparticles (HSNs) were formed, collected by centrifugation and washed with ethanol twice. The product (PEGs-ASNase@PEG-HSN 15) was finally dispersed and stored in 99.5% ethanol. The PEG-ASNase was encapsulated within the space between the inner and outer layers.

Example 1B

A control group of the hollow silica nanoparticles containing no ASNase (PEG-HSN 18) was prepared with a similar procedure to that described in Example 1A above, except that ASNase is not included in the aqueous phase.

Example 1C

PEGs-ASNase@PEG-HSN 10

Twenty (20) mL decane (as an oil phase), 3.5 mL CO-520 (as a surfactant) and 1.1 mL hexyl alcohol (as an optional co-surfactant) were mixed. Then, 350 μL $H_2O$ with 669.5 μg of PEGs-ASNase was added to the solution (as aqueous phase containing bioactive ingredient). After 2 minutes, 200 μL of TEOS and 25 μL of ethanolic APTMS solution (from a stock solution of 200 μL APTMS in 1.4 mL ethanol) (as an alkoxysilane and/or silica source) were added to the microemulsion and the microemulsion was stirred at 20° C. Fifteen minutes later, 500 μL of $NH_4OH$ (28-30 wt. %) (as an initiating reagent) was added dropwise to the microemulsion to initiate the hydrolysis of the silica alkoxysilane and/or silica source and form a silica nano-core. After 2 hrs., 350 μL $H_2O$ with 669.5 μg of PEGs-ASNase (as aqueous phase containing bioactive ingredient) was slowly added to the microemulsion. Another 10 minutes later, 300 µL of TEOS and 100 µL of ethanolic APTMS solution (as an alkoxysilane and/or silica source) were added to the microemulsion and the microemulsion was stirred for 12 hrs. at 20° C. to form a second silica layer enclosing the silica nano-core. Then, 500 µL of PEG-trimethoxysilane and 50 µL of TEOS were added to both of them to modify the surface of the silica nanoparticles. After 24 hrs., 95% ethanol was used to destabilize the microemulsion system. The resulting particles were collected by centrifugation at 15,500 rpm for 25 minutes and quickly rinsed with ethanol twice. Then, the particles were transferred into 200 mL D.I. water for washing at 50° C. for 2 hrs. Finally, the hollow silica nanoparticles (HSNs) were formed, collected by centrifugation and washed with ethanol twice. The product (PEGs-ASNase@PEG-HSN 10) was finally dispersed and stored in 99.5% ethanol. The PEG-ASNase was encapsulated within the space within the inner layer as well as the space between the inner and outer layers.

Synthesis of PEGs-HSN with TA-trimethoxysilane Surface Modification

Example 1D

PEGs-ASNase@PEG-HSN 17

Preparation of silica nanoparticles with TA-trimethoxysilane surface modification with N-[3-(trimethoxysilyl)propyl]-trimethylammonium chloride is illustrated below. Twenty (20) mL decane (as an oil phase), 3.5 mL CO-520 (as a surfactant) and 1.1 mL hexyl alcohol (as an optional co-surfactant) were mixed. Then, 200 µL of TEOS and 25 µL of ethanolic APTMS solution (from a stock solution of 200 µL APTMS in 1.4 mL ethanol) (as an alkoxysilane and/or silica source) were added to the mixture and the mixture was stirred at 20° C. Fifteen minutes later, 500 µL of $NH_4OH$ (28-30 wt. %) (as an initiating reagent) was added dropwise to the mixture to initiate the hydrolysis of the silica alkoxysilane and/or silica source and form a silica nano-core for 2 hrs. Then, 100 µL of N-[3-(trimethoxysilyl)propyl]-trimethylammonium chloride (TA-trimethoxysilane, 95%) was introduced after hydrolysis of silica alkoxysilane and/or silica source and stirred for 2 hrs. Then, 700 µL of $H_2O$ (with 2385.2 µg of PEGs-ASNase therein, as an aqueous phase) was slowly added into the microemulsion. Further 10 minutes later, 300 µL of TEOS and 100 µL of ethanolic APTMS solution (as an alkoxysilane and/or silica source) were added to the microemulsion, and the microemulsion was stirred for 12 hrs. at 20° C. to form a second silica layer enclosing the nano-core. Then, 500 µL of PEG-trimethoxysilane and 50 µL of TEOS were added to both of them to modify the outer surface of the particles. After 24 hrs., 95% ethanol was used to destabilize the microemulsion system. The particles was collected by centrifugation at 15,500 rpm for 25 minutes and quickly rinsed with ethanol twice. Then the particles were transferred into 200 mL D.I. water and washed at 50° C. for 2 hrs. Finally, the HSNs were formed, collected by centrifugation and washed with ethanol twice. The product (PEGs-ASNase@PEG-HSN 17) was finally stored in 99.5% ethanol.

Example 1E

A control group of the hollow silica nanoparticles where no ASNase is contained (PEG-HSN 19) is provided by a similar procedure to that described in Example 1D above, except that ASNase is not included in the aqueous phase.

Example 1F

PEGs-ASNase@PEG-HSN 11

Preparation of silica nanoparticles with TA-trimethoxysilane surface modification with N-[3-(trimethoxysilyl)propyl]-trimethylammonium chloride is illustrated below. Twenty (20) mL decane (as an oil phase), 3.5 mL CO-520 (as a surfactant) and 1.1 mL hexyl alcohol (as an optional co-surfactant) were mixed. Then, 350 µL $H_2O$ with 669.5 µs of PEGs-ASNase was added to the mixture (as an aqueous phase containing bioactive ingredient). After 2 minutes, 25 µL of N-[3-(trimethoxysilyl)propyl]-trimethylammonium chloride (TA-trimethoxysilane, 95%) was introduced to the microemulsion. Then, 200 µL of TEOS and 25 µL of ethanolic APTMS solution (200 µL APTMS in 1.4 mL ethanol) (as an alkoxysilane and/or silica source) were added to the microemulsion and the microemulsion was stirred at 20° C. Fifteen minutes later, 500 µL of $NH_4OH$ (28-30 wt. %) (as an initiating reagent) was added dropwise to the microemulsion to initiate the hydrolysis of the silica alkoxysilane and/or silica source and form a silica nano-core for 2 hrs. Then, 25 µL of N-[3-(trimethoxysilyl)propyl]-trimethylammonium chloride (TA-trimethoxysilane, 95%) was introduced after hydrolysis of silica alkoxysilane and/or silica source and stirred for 2 hrs. Then, 350 µL of $H_2O$ (with 669.5 µg of PEGs-ASNase therein, as an aqueous phase) was slowly added to the microemulsion. Another 10 minutes later, 300 µL of TEOS and 100 µL of ethanolic APTMS solution (as an alkoxysilane and/or silica source) were added to the microemulsion, and the microemulsion was stirred for 12 hrs. at 20° C. to form a second silica layer enclosing the nano-core. Then, 500 µL of PEG-trimethoxysilane and 50 µL of TEOS were added to both of them to modify the outer surface of the particles. After 24 hrs., 95% ethanol was used to destabilize the microemulsion system. The particles were collected by centrifugation at 15,500 rpm for 25 minutes and quickly rinsed with ethanol twice. Then the particles were transferred into 200 mL D.I. water and washed at 50° C. for 2 hrs. Finally, the HSNs was formed, collected by centrifugation and washed with ethanol twice. The product (PEGs-ASNase@PEG-HSN 11) was finally dispersed and stored in 99.5% ethanol. The PEG-ASNase was encapsulated within the space within the inner layer as well as the space between the inner and outer layers.

PEG-HSNs encapsulating bioactive agents and having a single layer were also prepared by using different conditions of washing.

The product yields of the particles obtained by these synthetic procedures are each about 100 mg/20 mL oil.

Example 2

TEM and DLS Measurements

The hollow silica nanoparticles as synthesized in Example 1 were subject to TEM measurements and the results are shown in FIG. 1. It can be observed that two-layered hollow silica nanoparticles, where each layer defines a closed hollow space, were successfully prepared. The particle sizes and standard deviations thereof are shown in Table 1.

TABLE 1

| Sample | Size ± SD (nm) |
| --- | --- |
| 10 | Second: 64.0 ± 6.0<br>First: 28.1 ± 4.3 |
| 11 | Second: 90.0 ± 11.1<br>First: 48.4 ± 10.5 |
| 18 (control) | Second: 86.24 ± 9.3<br>First: 38.82 ± 6.0 |
| 15 | Second: 83.74 ± 8.4<br>First: 38.85 ± 8.1 |
| 19 (control) | Second: 97.20 ± 11.4<br>First: 36.00 ± 6.4 |
| 17 | Second: 94.32 ± 6.3<br>First: 42.48 ± 4.2 |

TEM results suggest that PEGs-ASNase@PEG-HSN 10, 11, 15 and 17 have an average particle size of around 60 to 95 nm and small standard deviations of particle size, which reflect the uniformity of the particles and the superiority of the preparation methods disclosed in the present invention.

The particle size of the hollow silica nanoparticles measured via Dynamics Light Scattering (DLS) in different solution environments is shown in Table 2.

TABLE 2

| | Solution | | | | |
| --- | --- | --- | --- | --- | --- |
| Sample | $H_2O$ | DMEM + 10% FBS | DMEM + 20% FBS | RPMI + 10% FBS | PBS |
| 10 | 83.0 | 72.9 | | | 81.8 |
| 11 | 96.8 | 87.0 | | | 94.4 |
| 18 (control) | 95.21 | 79.4 | 63.2 | 66.8 | 95.9 |
| 15 | 105 | 100.7 | 80.3 | 86.2 | 106.1 |
| 19 (control) | 119.7 | 102.6 | 92.7 | 109.9 | 114.4 |
| 17 | 258.9 | 223.6 | 167.9 | 239.1 | 250.4 |

Unit: nm

DLS results show that PEG-HSNs 18 and 19 and PEGs-ASNase@PEG-HSNs 10, 11 and 15 dispersed well within the range from about 60 to about 110 nm in serum containing medium, which is deemed very suitable for cellular uptake. Though enlargement of particle size of PEGs-ASNase@PEG-HSN 17 occurs, which may be caused due to the high zeta potential of the particle resulted by the surface modification, the size is still acceptable for cellular uptake.

Nitrogen Sorption Isotherms and BET Surface Areas

Figure 2A:
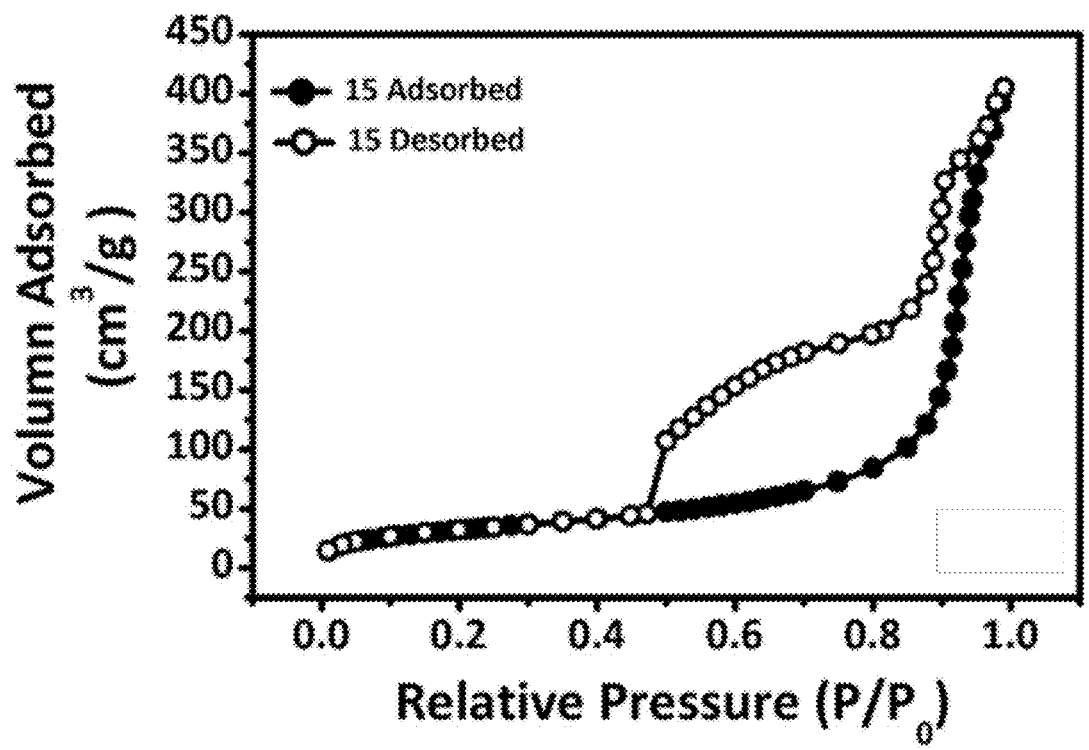
Figure 2B:
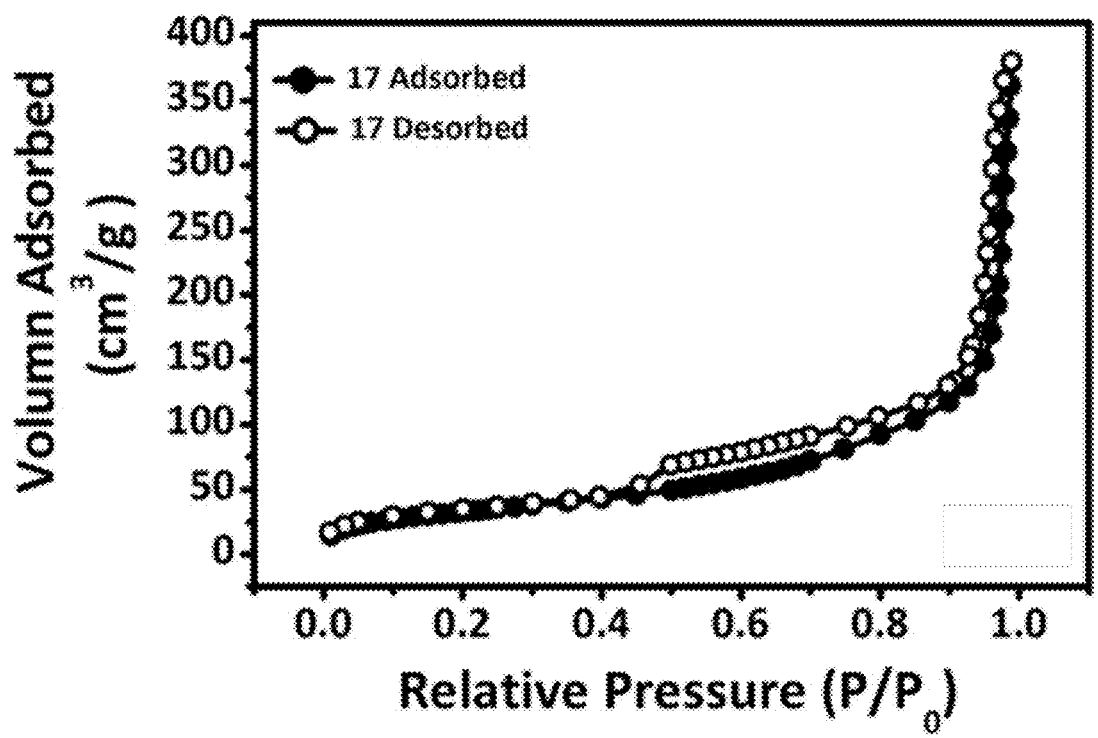

FIG. 2 shows nitrogen sorption isotherms of PEGs-ASNase@PEG-HSN 15 and PEGs-ASNase@PEG-HSN 17. Based on the isotherms, it is revealed that the BET surface area of PEGs-ASNase@PEG-HSN 15 and PEGs-ASNase@PEG-HSN 17 were 117.40 m$^2$/g and 120.00 m$^2$/g, respectively.

Example 3

Enzyme activity of free ASNases and ASNases encapsulated in the silica nanoparticles are acquired to evaluate the potential treating effect of the silica nanoparticles, with the methodology described above.

Figure 3A:
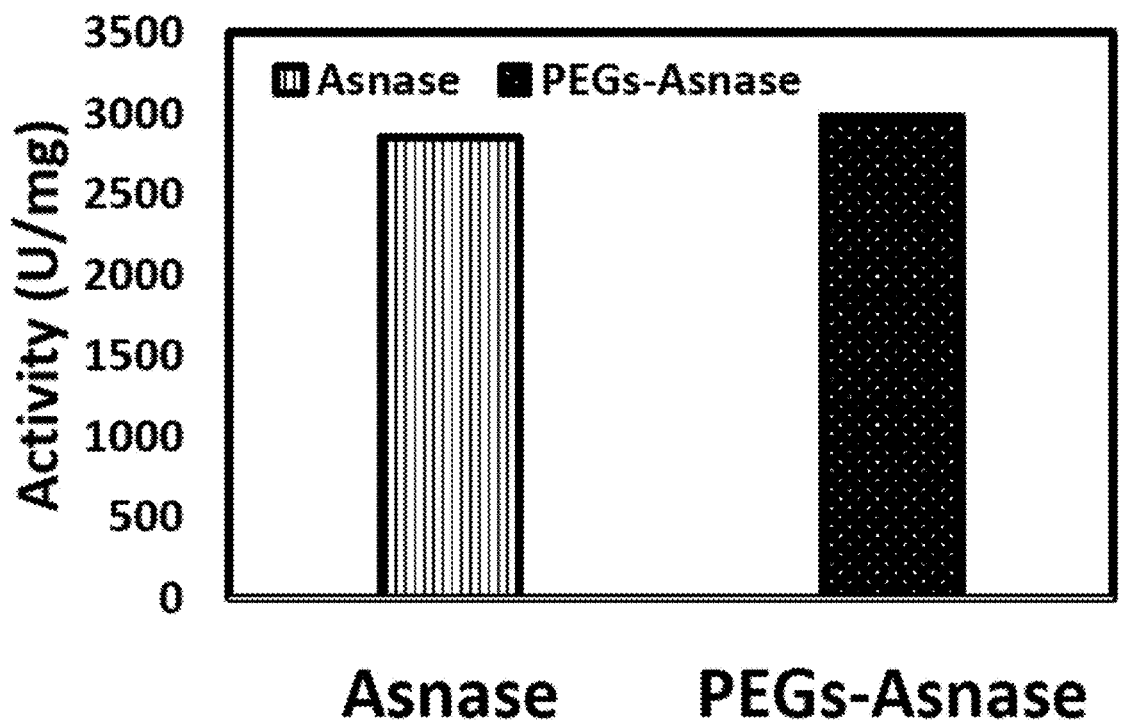

FIG. 3(A) shows the results of the enzyme activity of free ASNase and PEGs-ASNase. It is observed that free and modified ASNases show similar enzyme activity, which implies that the surface modification of ASNase for increasing water solubility and the probability of conjugation between PEGs-ASNase and silica sources would not influence the ASNase activity.

Figure 3B:
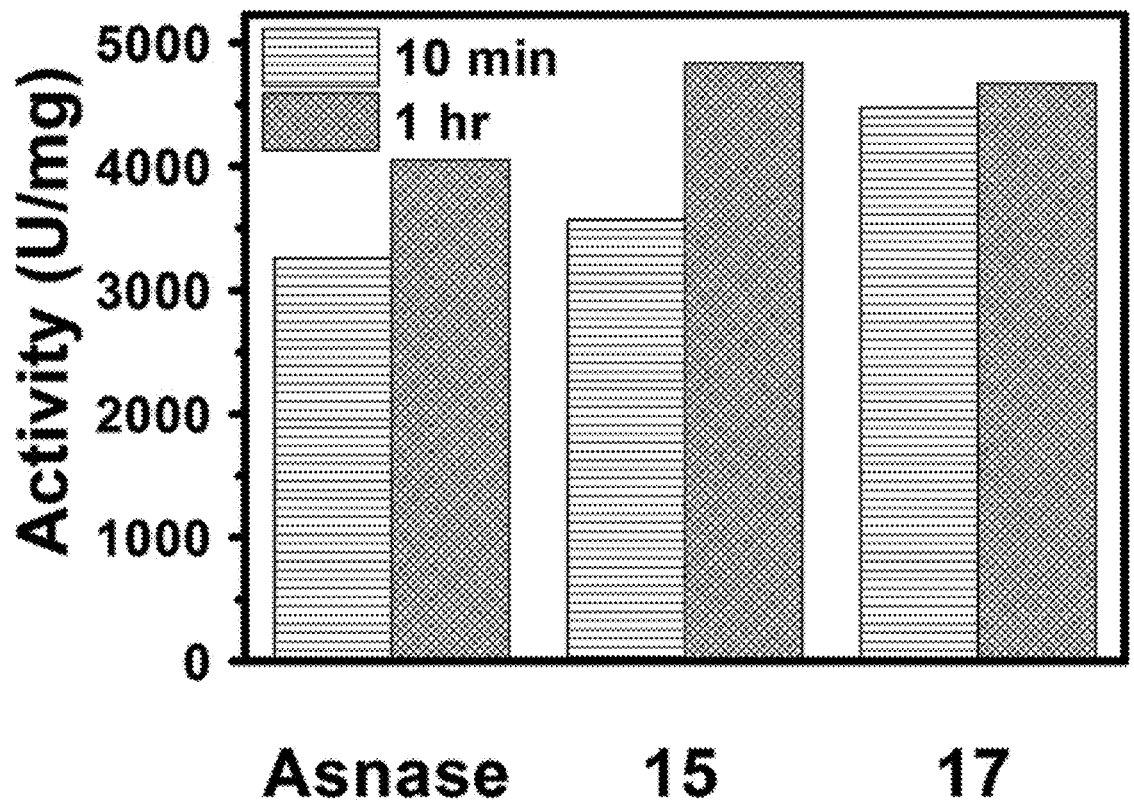

FIG. 3(B) shows the results of the enzyme activity of PEGs-ASNase, PEGs-ASNase@PEG-HSN 15 and PEGs-ASNase@PEG-HSN 17. It is observed that the enzymatic activity of PEGs-ASNase@PEG-HSN 15 and PEGs-ASNase@PEG-HSN 17 were similar to that of the free ASNase either measured upon 10 mins or 1 hr. These results reveal that the activity of ASNase encapsulated in HSN was not significant changed, which ensures validity of the silica nanoparticles in the expression of enzyme activity in treatments.

Example 4

Trypsin Tolerance Assay

As known in the art, one of the side effects of the ASNase treatment is acute pancreatitis, which causes the release of trypsin from pancreas and results in elevated trypsin in the blood. Accordingly, the ASNases are more easily subject to trypsin degradation. To determine the protective effect of the silica nanoparticles disclosed herein on the ASNase encapsulated therein from trypsin degradation, free ASNases or ASNases encapsulated in silica nanoparticles were subjected to trypsin digestion, and the remaining ASNase activity was determined by ASNase activity assay. Hence, trypsin tolerance tests are performed to evaluate the protective effect of the silica nanoparticles on the ASNases encapsulated therein.

Free ASNases and ASNases encapsulated in PEG-HSN, all containing 0.8 U of ASNases, were centrifuged and dispersed in 200 μL of Tris buffer (0.05 M, pH 8.6), mixed with trypsin (1.5 U per 40 μL in $NaH_2PO_4$ buffer solution), and subjected to trypsin digestion at 37° C. for 2 hours. After digestion, the ASNase activity in the samples was determined by ASNase activity assay.

The following groups were subjected to trypsin tolerance assay: free ASNase, PEG-trimethoxysilane modified ASNase ("PEGs-ASNase") encapsulated in the double-layered PEG-HSN without TA modification ("PEGs-ASNase@PEG-HSN 15"), PEG-trimethoxysilane modified ASNase encapsulated in the double-layered PEG-HSN with TA modification ("PEGs-ASNase@PEG-HSN 17"), wherein all groups contain 0.8 U of ASNase. The relative ASNase activity of each group compared to the control group (free ASNases without being digested by trypsin) was determined. The results showed that both PEGs-ASNase@PEG-HSN 15 and 17 are able to reach approximately 100% relative activity within 6 hours. In contrast, after digestion, free ASNases can only reach 10% relative ASNase activity within 8 hours. Given the above, ASNases encapsulated in the double-layered silica nanoparticles were more resistant to trypsin digestion compared with free ASNases. The results revealed that the silica nanoparticles disclosed herein are able to provide excellent protective effect on the proteins/enzymes encapsulated therein from protease degradation.

Example 5

As known in the art, depletion of L-asparagine causes protein synthesis inhibition in tumor cells (such as acute leukemic cells) thereby resulting in cell death. The cytotoxicity of the ASNase encapsulated in the silica nanoparticles was tested by the following experiments:

Cell Culture

MOLT-4 and Jurkat cells (both are human acute lymphoblastic leukemia suspension cell line, obtained from the Bioresource Collection and Research Center (Taiwan)), 4T1

(mouse mammary gland cancer cell line, this tumor is an animal stage IV human breast cancer; obtained as a gift from another laboratory) and A549 (human lung cancer cell line, obtained as a gift from another laboratory) were incubated in RPMI-1640 medium with 10% fetal bovine serum (FBS), BxPc-3 (human pancreatic cancer cell line) obtained from the Bioresource Collection and Research Center (Taiwan) were incubated in RPMI-1640 medium with 10 mM HEPES, 1 mM sodium pyruvate and 10% fetal bovine serum (FBS) at 37° C. in a humidified 5% $CO_2$ atmosphere, and all the aforementioned media contained 100 U/mL penicillin and 100 μg/mL streptomycin. When the suspension cells reached about 60-70% confluence, they were harvested for subculture.

Cytotoxicity Assay (by WST-1 Assay)

Figure 4:
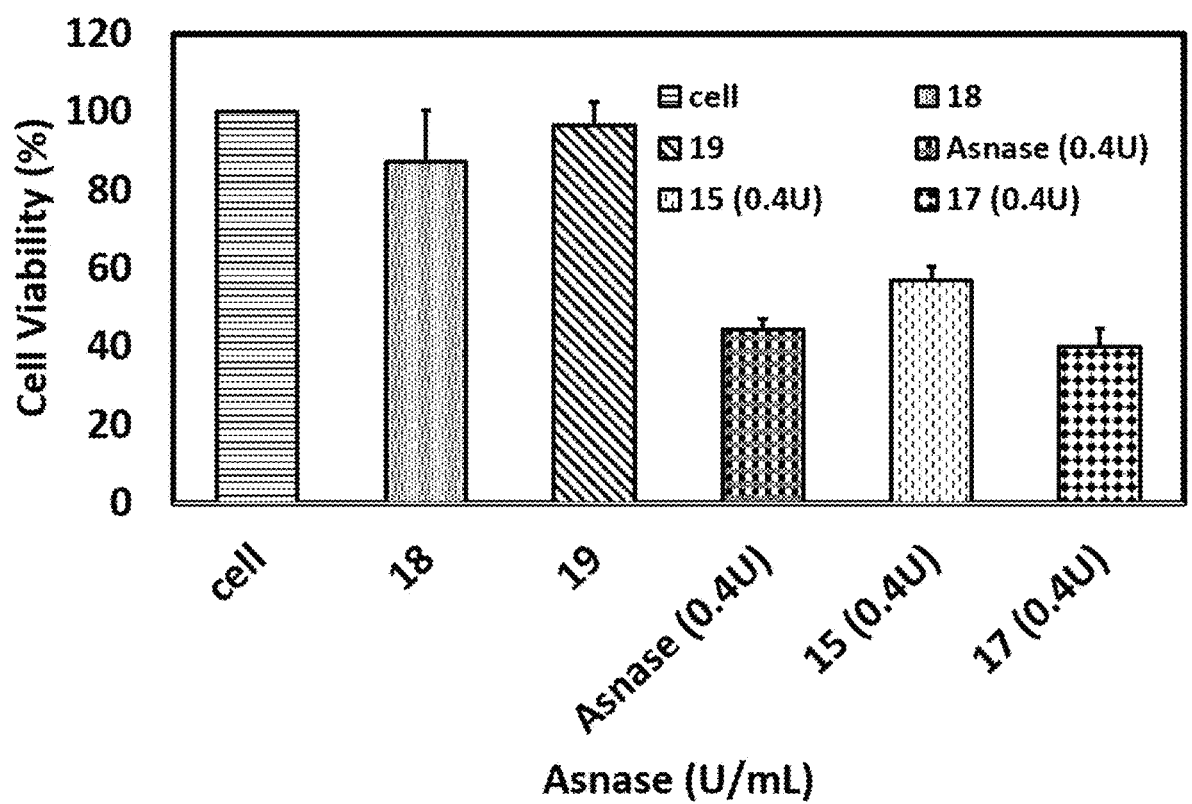

In this experiment, the leukemic cell lines (MOLT-4 and Jurkat), breast cancer cell line (4T1) and pancreatic cell line (BxPc-3) were treated with free ASNase, PEGs-ASNase@PEG-HSN 15 and 17 containing 0.4, 0.4, 0.2, or 1 U/mL of ASNase respectively. The PEG-HSN 18 and 19 were treated as control groups (control groups of PEGs-ASNase@PEG-HSN 15 and 17 without ASNase). In particular, $4 \times 10^5$ cells per well of acute leukemic cells (MOLT-4 and Jurkat) and $2 \times 10^4$ cells per well of 4T1 cell line were seeded in a 24-well plate and treated with the aforementioned groups for 24 or 72 hours. $4 \times 10^3$ cells per well of pancreatic cell line (BxPc-3) was seeded in a 96-well plate and treated with the aforementioned groups for 48 hours. The cells were then incubated with WST-1 reagent (Clontech) at 37° C. for 30 minutes, and the absorbance at 450 nm was measured to detect the yellow formazan dye produced by the living cells by a microplate reader (Bio-Red, model 680). The cells without any treatment were used as a 100% cell viability control. As shown in FIG. 4, both PEGs-ASNase@PEG-HSN 15 and 17 exhibited excellent cytotoxicity against the MOLT-4 leukemic cell line comparable to free ASNase. The results showed that encapsulating the ASNase by the silica nanoparticles did not significantly influence the bioactivity thereof. In addition, since both PEG-HSN 18 and 19 did not exhibit obvious cytotoxicity, it is believed that the cytotoxicity of PEGs-ASNase@PEG-HSN 15 and 17 was attributed solely to ASNase. In addition to the MOLT-4 leukemic cell line, we also conducted cytotoxicity assay of Jurkat leukemic cell line, 4T1 breast cancer cell line and BxPc-3 pancreatic cancer cell line. The results showed that both PEGs-ASNase@PEG-HSN 15 and 17 exhibited cytotoxicity against these cancer cell lines.

Example 6

Cellular Uptake Assays

Figure 5A:
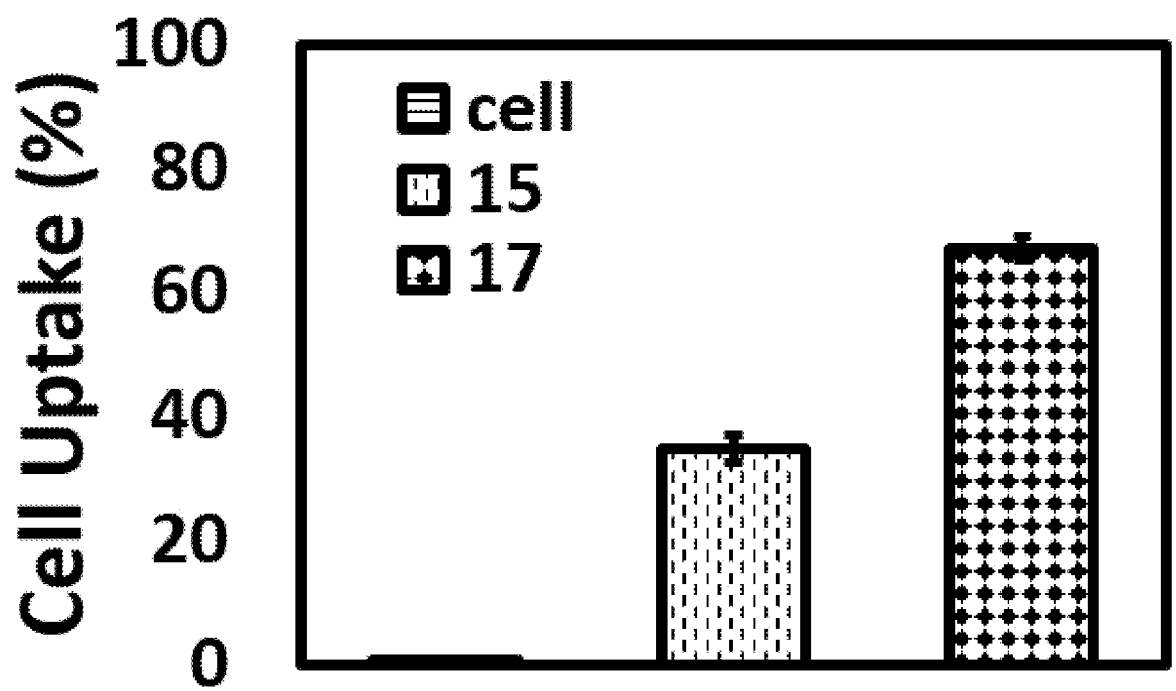
Figure 5:
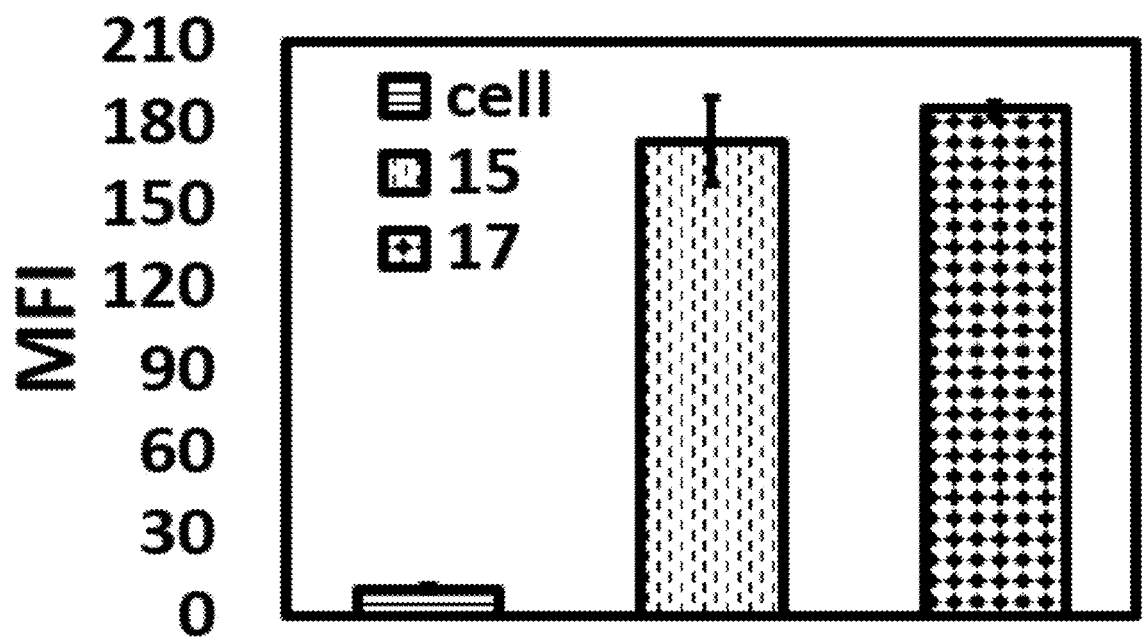
Figure 6C:
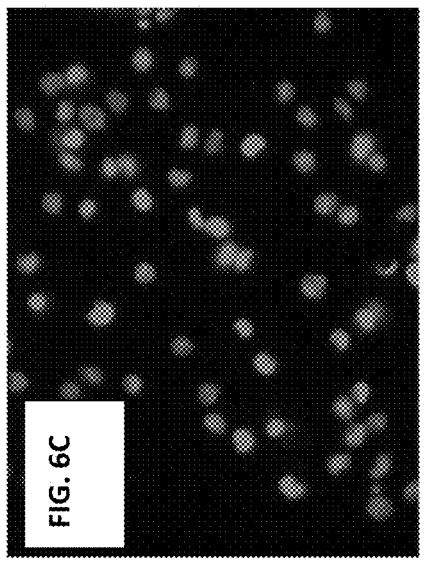
FIG. 6A-6F shows the results of tests of the ability to induce apoptosis of MOLT-4 leukemic cell line with free ASNase, control silica nanoparticles and the inventive silica nanoparticles.
Figure 6B:
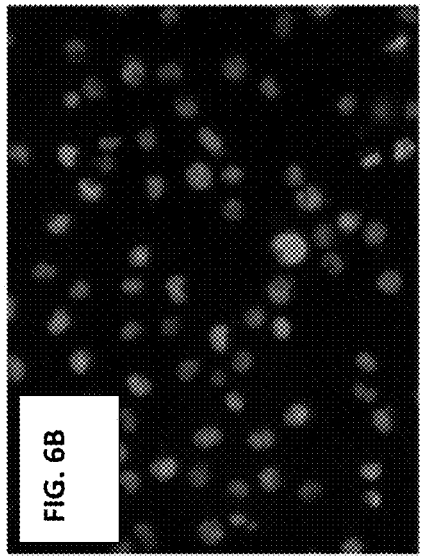
Figure 6A:
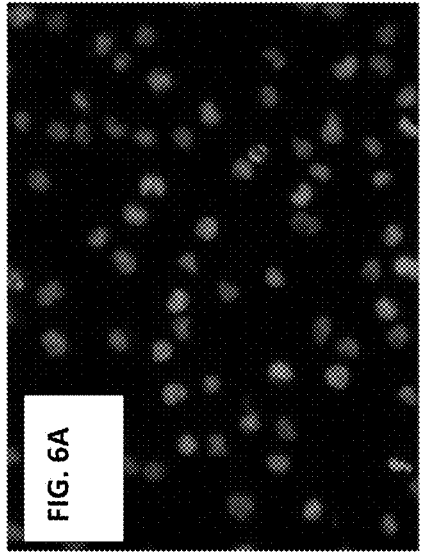
Figure 6F:
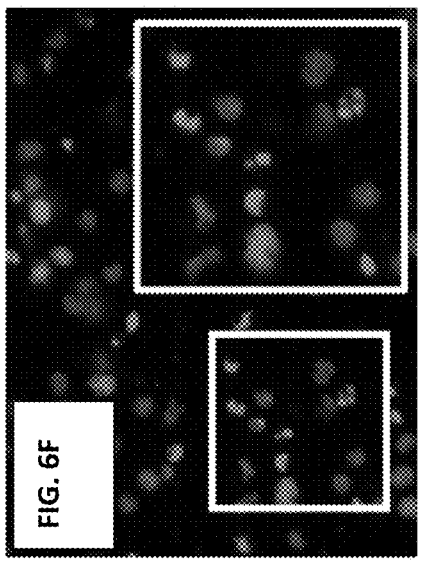
Figure 6E:
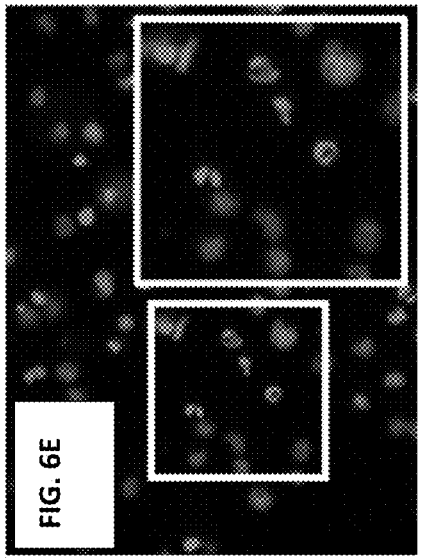
Figure 6D:
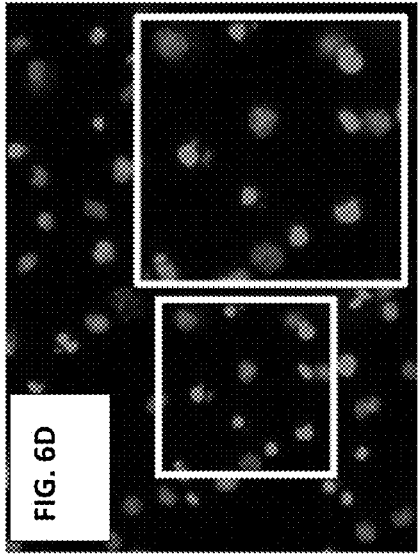

The cellular uptake efficiency of the silica nanoparticles by MOLT-4 and A549 cells was determined by a FACS Calibur flow cytometry (BD Biosciences). The red emitting fluorescein dye (rhodamine-B-isothiocyanate; RITC) conjugated to the ASNase in the silica nanoparticles served as a marker to quantitatively determine the cellular uptake efficiency of the particle. The cell culture condition of MOLT-4 and A549 cells was the same as that described in Example 5. In particular, $1 \times 10^6$ of MOLT-4 cells or $2 \times 10^5$ of A549 cells per well were seeded in 6-well plates and incubated with PEGs-ASNase@PEG-HSN 15 and 17 (0.9 mg particles/mL) in serum-containing medium for 24 hours. The cells were then washed twice with PBS, harvested, centrifuged, and subjected to flow cytometry analysis to detect the fluorescence signal thereof. The cellular uptake ratio was calculated by the ratio of the cells with fluorescence signal and total cells; the mean fluorescence intensity (MFI) was the mean value of the fluorescence intensity of the cells having fluorescence signal. As shown in FIG. 5(A), both PEGs-ASNase@PEG-HSN 15 and 17 exhibited good cellular uptake efficiency in MOLT-4 leukemic cell line, and the cellular uptake efficiency of TA-trimethoxysilane modified silica nanoparticle PEGs-ASNase@PEG-HSN 17 was higher. Without being bound to theory, the more positively-charged PEGs-ASNase@PEG-HSN 17 caused by TA modification made the silica nanoparticles more easily uptaken by cells. The results also showed that different modifications made to the silica nanoparticles may be used to adjust its properties such as cellular uptake efficiency. As shown in FIG. 5(B), the mean fluorescence intensity (MFI) of the two groups were similar. In addition to the MOLT-4 leukemic cell line, it was also proven that PEGs-ASNase@PEG-HSN 15 and 17 were able to be uptaken by the A549 lung cancer cell line (a solid tumor cell line).

Example 7

Apoptosis Assays

To investigate the effect of the treatment of ASNases on the level of apoptosis, $1 \times 10^6$ MOLT-4 cells (the cell culture condition of MOLT-4 was the same as that described in Example 2) were seeded in a 6-well plate and treated with free ASNase, PEGs-ASNase@PEG-HSN 15 and 17 containing 0.4 U/mL of ASNase, and PEG-HSN 18 and 19 (control groups of PEGs-ASNase@PEG-HSN 15 and 17, without encapsulating ASNases) at 37° C. in serum-containing medium for 24 hours. The cells were harvested by centrifugation (400 g, 10 minutes, at 4° C.), washed with PBS, stained with 4'6-diamidino-2-phenylindole dihydrochloride (DAPI; 1 μg/mL) for 10 minutes, washed with PBS again, and re-suspended in 1 mL of PBS in a 6-well plate. The nuclear morphology changes and apoptotic bodies (caused by DNA fragmentation) of the cells were observed under an inverted fluorescence microscope (Olympus, magnification 40×, mercury lamp for UV excitation). As shown in FIG. 6, the MOLT-4 cells treated with free ASNase (d)) and PEGs-ASNase@PEG-HSN 15 and 17 (e) and f)) exhibited apoptotic signs. The results suggest that ASNases encapsulated in the silica nanoparticles disclosed herein exhibited efficacy in inducing apoptosis similar to free ASNases.

Example 8

Clearance of Silica Nanoparticles from Circulation

Figure 7:
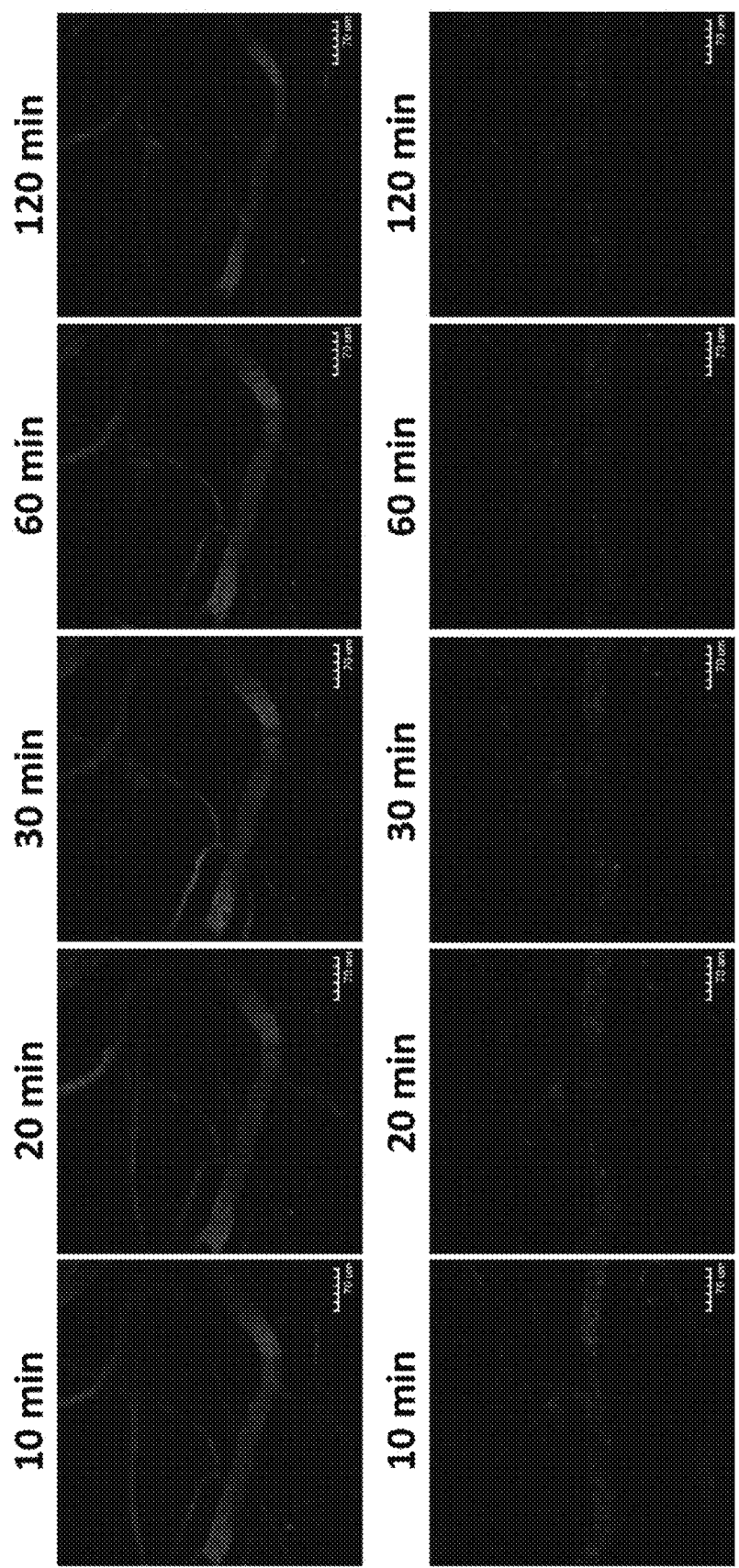
FIG. 7 shows the results of the clearance from circulation of the inventive silica nanoparticles in mice.

PEGs-ASNase@PEG-HSN (having RITC conjugated with ASNase) was used to investigate its clearance rate from circulation in mice. In particular, 4T1 tumor bearing BALB/c nude mice (8 weeks old) were intravenously injected with PEGs-ASNase@PEG-HSN 15 and 17 (in PBS, 30 mg/mL dose). The blood vessels in the ears of the mice were observed under two-photon microscopy, and the real-time images were acquired at 10, 30, 60 and 120 minutes after injection. As shown in FIG. 7, the signal of PEGs-ASNase@PEG-HSN 15 decayed very slowly (even after 120 minutes from injection, the signal could still be detected) (upper row of FIG. 7); in contrast, the fluorescence signal from PEGs-ASNase@PEG-HSN 17 was much weaker even at the same time points (lower row of FIG. 7). The longer circulation time indicates a longer half-life in blood. The results suggest that more positively-charged PEGs-ASNase@PEG-HSN 17 (with TA-trimethoxy silane modification) is more easily cleared from the blood. It can be inferred that modifications, such as TA modification, could be used to adjust the half-life of the silica nanoparticles in blood. In addition, despite the different circulation time in blood, both PEGs-ASNase@PEG-HSN 15 and 17 dispersed well and did not form obvious aggregates in blood, which suggests that the silica nanoparticles have good stability in vivo.

Example 9

Bio-Distribution Assays

Figure 8:
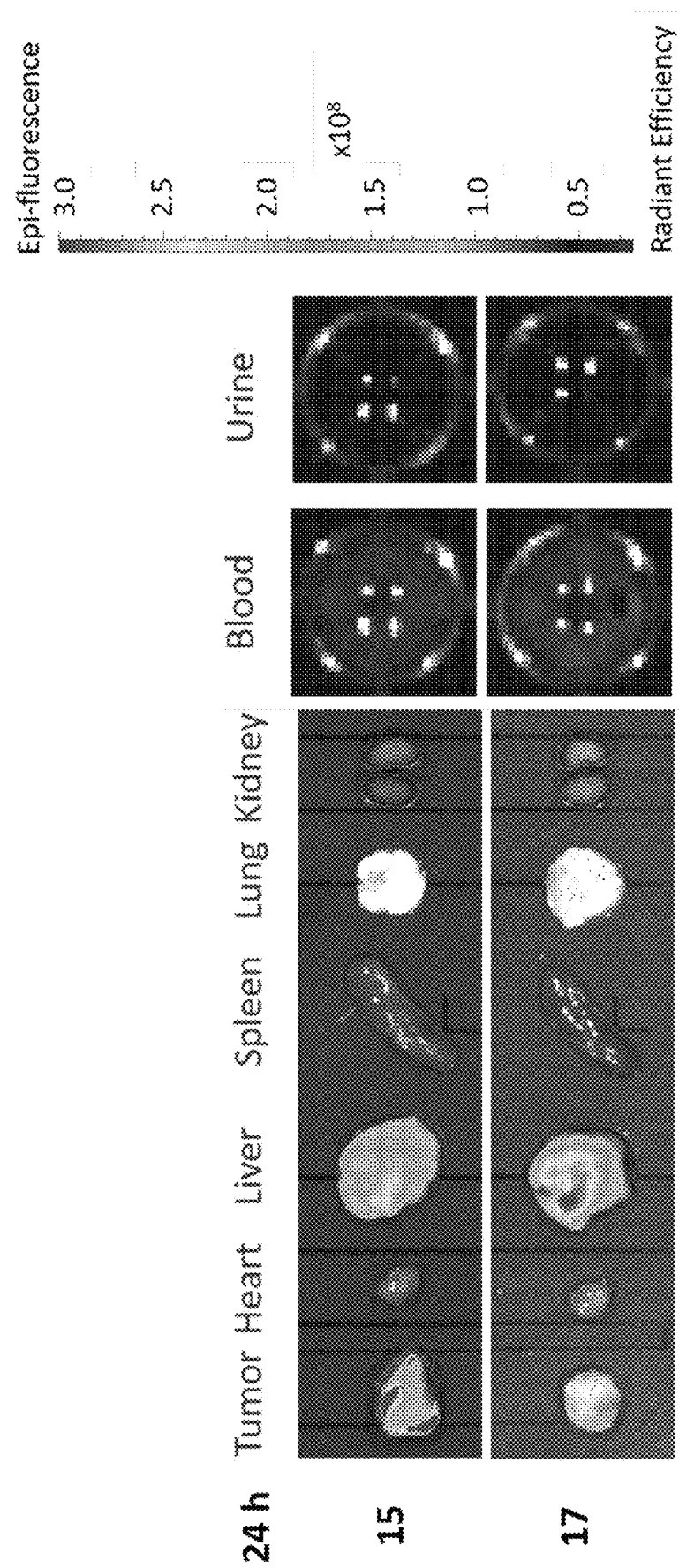
FIG. 8 shows the results of bio-distribution analysis of the inventive particles by IVIS fluorescence imaging system.

Tumor bearing BALB/c nude mice (9 weeks old) were intravenously injected with PEGs-ASNase@PEG-HSN 15 and 17 (in PBS, 30 mg/mL dose). The bio-distribution of the silica nanoparticles in the major organs (including heart, lung, spleen, liver and kidney), the tumor, urine and blood were observed under IVIS fluorescence imaging system (Lumina), after 24 hours of the injection. As shown in FIG. 8, PEGs-ASNase@PEG-HSN 15 (the upper row) and 17 (the lower row) were mainly trapped in the tumor and liver as well as the liver, respectively; both nanoparticles could be found in the kidney; no significant signal was observed in urine and blood. The results showed that PEGs-ASNase@PEG-HSN 15 could be more easily trapped in the tumor tissue and provided an effective way to deliver bioactive ingredients to the tumor; the results also suggest that PEGs-ASNase@PEG-HSN 15 rendered excellent enhanced permeability and retention (EPR) effects on the nanoparticles to keep them accumulated in the tumor. It is believed that the low accumulation in the tumor of PEGs-ASNase@PEG-HSN 17 resulted from its rapid clearance from circulation. The results suggest that modifications (such as a TA modification) could be used to adjust the bio-distribution profile of the silica nanoparticles.

A person of ordinary skill in the art of the subject invention should understand that variations and modification may be made to the teaching and the disclosure of the subject invention without departing from the spirit and scope of the subject application. Based on the contents above, the subject application intends to cover any variations and modification thereof with the proviso that the variations or modifications fall within the scope as defined in the appended claims or their equivalents.

We claim:

1. A silica nanoparticle, comprising
   a plurality of layered silica shells, wherein each shell has meso-pores and encloses a closed hollow space, optionally the innermost hollow closed space has a solid silica core, wherein the space is defined by the distance between any two silica shells or the solid silica core; and
   one or more bioactive ingredients encapsulated within the space, wherein the bioactive ingredient has a size larger than the pore size of the shell encapsulating it, and wherein the bioactive ingredient in each space may be the same or different.

2. The silica nanoparticle according to claim 1, which has a particle size ranging from about 20 nm to about 500 nm.

3. The silica nanoparticle according to claim 1, which has a particle size ranging from about 20 nm to about 150 nm.

4. The silica nanoparticle according to claim 1, which has two or more shells.

5. The silica nanoparticle according to claim 1, wherein each shell has organosilica residues.

6. The silica nanoparticle according to claim 1, wherein the pore size of the shell is less than 5 nm.

7. The silica nanoparticle according to claim 1, wherein the shells each independently have a thickness of about 2 nm to about 15 nm.

8. The silica nanoparticle according to claim 1, wherein the size of the space is adjustable.

9. The silica nanoparticle according to claim 1, wherein the distance between the shells ranges from 2 nm to 75 nm.

10. The silica nanoparticle according to claim 1, wherein the bioactive ingredient with or without a surface modification can be dispersed in or dissolved in an aqueous phase.

11. The silica nanoparticle according to claim 1, wherein the bioactive ingredient is an enzyme, a protein drug, an antibody, a vaccine, an antibiotic or a nucleotide drug.

12. The silica nanoparticle according to claim 11, wherein the enzyme is agalsidase, imiglucerase, taliglucerase, velaglucerase, alglucerase, sebelipase, laronidase, idursulfase, elosulfase, galsulfase, alglucosidase, asparaginase, glutaminase, arginine deiminase, arginase, methioninase, cysteinase, homocysteinase, phenylalanine hydroxylase, phenylalanine ammonia lyase, urate oxidase, catalase, horseradish peroxidase, superoxide dismutase or glutathione peroxidase.

13. The silica nanoparticle according to claim 1, wherein a poly(ethylene glycol) (PEG) or a tumor targeting ligand is optionally linked to the outer surface of each shell.

14. A method for preparing a silica nanoparticle, comprising the steps of:
   (a) any one of steps (a-1) and (a-2):
      (a-1) providing an oil phase, a surfactant, an alkoxysilane and/or silicate source, an aqueous phase optionally containing one or more bioactive ingredients and optionally a co-surfactant to form a water-in-oil (W/O) microemulsion; and
      (a-2) providing an oil phase, a surfactant, an alkoxysilane and/or silicate source and optionally a co-surfactant to form a mixture;
   (b) adding an initiating reagent to the W/O microemulsion of (a-1), or adding an aqueous initiating reagent to the mixture of (a-2) to form a W/O microemulsion, and forming a silica nano-core which links the bioactive ingredient on the surface thereof and/or encapsulates the bioactive ingredient therein;
   (c) providing an aqueous phase containing a bioactive ingredient;
   (d) introducing an alkoxysilane and/or silicate source to form an additional silica layer enclosing the silica nano-core of (b);
   (e) optionally repeating the steps (c) and (d) one or more times;
   (f) performing a destabilizing condition to destabilize the W/O microemulsion and collecting the resulting particle thus formed from the microemulsion; and
   (g) dispersing the particle collected in step (f) in an aqueous washing phase to obtain the silica nanoparticle;
   wherein the alkoxysilane and/or silicate source in steps (d) and (e) and optionally that in step (a) comprise at least one organo-alkoxysilane, and
   wherein the size of the bioactive ingredients is larger than the pore size of the silica shell encapsulating the same.

15. The method according to claim 14, wherein the order of the introduction of the aqueous phase optionally containing one or more bioactive ingredients and the alkoxysilane and/or silicate source in step (a-1) can be reversed or done simultaneously.

16. The method according to claim 14, wherein the oil phase is dodecane, decane, octane, hexane, cyclohexane, benzene, toluene, xylene triglyceride oil or a plant oil.

17. The method according to claim 14, wherein the surfactant is a non-ionic surfactant.

18. The method according to claim 17, wherein the non-ionic surfactant is poly(oxyethylene)nonylphenyl ether, polyoxyethylene glycol sorbitan alkyl ester, polyethylene glycol alkyl ether, glucoside alkyl ether, polyethylene glycol octylphenyl ether, polyethylene glycol alkylphenyl ether, glycerol alkyl ester, polypropylene glycol alkyl ethers, block copolymers, poloxamers, cocamide MEA, cocamide DEA, lauryldimethylamine oxide or polyethoxylated tallow amine.

19. The method according to claim 14, wherein the alkoxysilane and/or silicate sources are each independently the same or different.

20. The method according to claim 14, wherein the alkoxysilane and/or silicate source comprises tetraethoxysilane (TEOS), tetramethoxysilane (TMOS), sodium silicate or a mixture thereof.

21. The method according to claim 14, wherein the organo-alkoxysilane is 2-[methoxy(polyethyleneoxy)propyl]-trimethoxysilane (PEG-trimethoxysilane), 3-aminopropyltrimethoxysilane (APTMS), propyl triethoxy silane, butyl trimethoxy silane, octyl trimethoxy silane, diphenyl diethoxy silane, n-octyl triethoxy silane, mercapto propyl trimethoxy silane, chloro methyl trimethoxy silane, isobutyl triethoxy silane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediamine triacetic acid (EDTAS), (3-trihydroxysilyl)propyl methylphosphonate (THPMP), methyltriacetoxysilane (MTAS), N-[3-(trimethoxysilyl)propyl] ethylenediamine, trimethoxysilylpropyl modified (polyethlenimine), (3-mercaptopropyl)trimethoxysilane (MPTMS), N-[3-(trimethoxysilyl)propyl]-N,N,N-trimethylammonium chloride, zwitterionic silane or a mixture thereof.

22. The method according to claim 14, wherein the alkoxysilane and/or silicate source is a mixture of TEOS and APTMS, a mixture of THPMP, APTMS and TEOS or a mixture of EDTAS, APTMS and TEOS.

23. The method according to claim 14, wherein when step (e) is employed, wherein the number of shells of the silica nanoparticles is determined by the alkoxysilane and/or silicate source, the time of washing and the temperature for conducting the washing.

24. The method according to claim 14, wherein the aqueous phase is water, aqueous buffer, aqueous DMSO solution or aqueous alkanolic solution or co-solvent containing solution.

25. The method according to claim 14, wherein the bioactive ingredients in steps (a), (c) and (e) are each independently the same or different.

26. The method according to claim 14, wherein the bioactive ingredient with or without surface modification can be dispersed or dissolved in an aqueous phase.

27. The method according to claim 14, wherein the bioactive ingredient is an enzyme, a protein drug, an antibody, a vaccine, an antibiotic or a nucleotide drug.

28. The method according to claim 27, wherein the enzyme is agalsidase, imiglucerase, taliglucerase, velaglucerase, alglucerase, sebelipase, laronidase, idursulfase, elosulfase, galsulfase, alglucosidase, asparaginase, glutaminase, arginine deiminase, arginase, methioninase, cysteinase, homocysteinase, phenylalanine hydroxylase, phenylalanine ammonia lyase, urate oxidase, catalase, horseradish peroxidase, superoxide dismutase or glutathione peroxidase.

29. A silica nanoparticle, which is prepared by the method of any of claims 14 to 28.

* * * * *